United States Patent
Kim

(10) Patent No.: US 12,036,265 B2
(45) Date of Patent: Jul. 16, 2024

(54) COMPOSITIONS AND METHODS RELATING TO BONE REPAIR AND REGENERATION

(71) Applicant: Wayne State University, Detroit, MI (US)

(72) Inventor: Hyeong-Reh C. Kim, Bloomfield, MI (US)

(73) Assignee: Wayne State University, Detroit, MI (US)

( * ) Notice: Subject to any disclaimer, the term of this patent is extended or adjusted under 35 U.S.C. 154(b) by 119 days.

(21) Appl. No.: 17/362,008

(22) Filed: Jun. 29, 2021

(65) Prior Publication Data

US 2021/0401936 A1      Dec. 30, 2021

Related U.S. Application Data

(60) Provisional application No. 63/045,473, filed on Jun. 29, 2020.

(51) Int. Cl.
| | |
|---|---|
| *A61K 38/18* | (2006.01) |
| *A61K 35/28* | (2015.01) |
| *A61K 47/64* | (2017.01) |
| *A61P 19/08* | (2006.01) |
| *C07K 14/49* | (2006.01) |

(52) U.S. Cl.
CPC .......... *A61K 38/1858* (2013.01); *A61K 35/28* (2013.01); *A61K 47/642* (2017.08); *A61P 19/08* (2018.01); *C07K 14/49* (2013.01)

(58) Field of Classification Search
None
See application file for complete search history.

(56) References Cited

U.S. PATENT DOCUMENTS

2006/0094647 A1*  5/2006  Jeffers .................. A61P 7/00
                                                              514/12.2

OTHER PUBLICATIONS

NCBI BLAST alignment tool, accessed at https://blast.ncbi.nlm.nih.gov/Blast.cgi, protein sequence alignment of SEQ ID No. 5 with PDGF-D amino acid sequence of Ustach Fig. 7B with mutations taught in Huang, performed Apr. 13, 2023 (Year: 2023).*
Rindone, A. et al., Heparin-Conjugated Decellularized Bone Particles Promote Enhanced Osteogenic Signaling of PDGF-BB to Adipose-Derived Stem Cells in Tissue Engineered Bone Grafts, Advanced Healthcare Materials, 8: e1801565, 2019.
Yu, J. et al., Platelet-derived Growth Factor Signaling and Human Cancer, Journal of Biochemistry and Molecular Biology, 36(1): 49-59, Jan. 2003.
Bayer, E. et al., The Influence of Platelet-Derived Growth Factor and Bone Morphogenetic Protein Presentation on Tubule Organization by Human Umbilical Vascular Endothelial Cells and Human Mesenchymal Stem Cells in Coculture, Tissue Engineering Part A, 22(21-22): 1296-1304, Oct. 10, 2016.
Shah, P. et al., A review of platelet derived growth factor playing pivotal role in bone regeneration, Journal of Oral Implantology, 40(3): 330-40, 2014.
Caplan, A. et al., PDGF in bone formation and regeneration: new insights into a novel mechanism involving MSCs, Journal of Orthopaedic Research, 29: 1795-1803, May 25, 2011.
Bergsten, E. et al., PDGF-D is a specific, protease-activated ligand for the PDGF beta-receptor, Nature Cell Biology, 3: 512-516, May 2001.
Larochelle, W. et al., PDGF-D, a new protease-activated growth factor, Nature Cell Biology, 3: 517-521, May 2001.
Li, X. et al., PDGF-C is a new protease-activated ligand for the PDGF alpha-receptor, Nature Cell Biology, 2: 302-309, May 2000.
Ustach, C. et al., Platelet-derived growth factor D is activated by urokinase plasminogen activator in prostate carcinoma cells, Molecular and Cellular Biology, 25(14): 6279-6288, Jul. 2005.
Ustach, C. et al., A novel signaling axis of matriptase/PDGF-D/β-PDGFR in human prostate cancer, Cancer Research, 70(23): 9631-9640, Dec. 1, 2010.
Hurst, N., Jr. et al., Platelet-derived growth factor-C (PDGF-C) activation by serine proteases: implications for breast cancer progression, The Biochemical Journal, 441(3): 909-918, Feb. 1, 2012.
Li, H. et al., PDGF-D is a potent transforming and angiogenic growth factor, Oncogene, 22(10): 1501-1510, Mar. 13, 2003.
Ehnman, M. et al., The uPA/uPAR system regulates the bioavailability of PDGF-DD: implications for tumour growth, Oncogene, 28: 534-544, Nov. 10, 2008.
Najy, A. et al., Differential tumorigenic potential and matriptase activation between PDGF B versus PDGF D in prostate cancer, Molecular Cancer Research: MCR, 10(8): 1087-1097, Aug. 2012.
Najy, A. et al., Matriptase activation and shedding through PDGF-D-mediated extracellular acidosis, Am J Physiol Cell Physiol, 310: C293-304, Jul. 8, 2015.
Huang, W. et al., Dynamic Regulation of Platelet-derived Growth Factor D (PDGF-D) Activity and Extracellular Spatial Distribution by Matriptase-mediated Proteolysis, J. Biol. Chem., 290(14):9162-9170, Feb. 12, 2015.
Feinberg, H. et al., Crystal structure of the CUB1-EGF-CUB2 region of mannose-binding protein associated serine protease-2, The EMBO Journal, 22(10):2348-2359, 2003.

(Continued)

*Primary Examiner* — Emily A Cordas
(74) *Attorney, Agent, or Firm* — Julie K. Staple; Dinsmore & Shohl LLP

(57) ABSTRACT

Methods of treating a subject in need thereof are provided which include: administering a recombinant platelet derived growth factor D (PDGF D) composition to a mesenchymal stem cell of the subject and/or a progenitor derived therefrom, in vivo, or ex vivo, producing a treated mesenchymal stem cell of the subject and/or a progenitor derived therefrom, thereby stimulating the mesenchymal stem cell (MSC) and/or a progenitor derived therefrom. Cells expressing a recombinant PDGF D composition of the present are administered to the subject for in vivo delivery of the recombinant PDGF D composition according to aspects of the present disclosure. Methods and compositions are provided including recombinant PDGF D hemidimer (HD) including a full-length PDGF D polypeptide and a C-terminal growth factor domain of PDGF D, which lacks a CUB domain, promoting regulation of bone marrow MSC differentiation into osteogenic lineage cells.

16 Claims, 16 Drawing Sheets

Specification includes a Sequence Listing.

(56) References Cited

OTHER PUBLICATIONS

Chu, V. T., et al., Efficient generation of Rosa26 knock-in mice using CRISPR/Cas9 in C57BL/6 zygotes, BMC Biotechnology, 16:4, DOI 10.1186/s12896-016-0234-4, 2016, 15 pages.

* cited by examiner

FIG. 9A
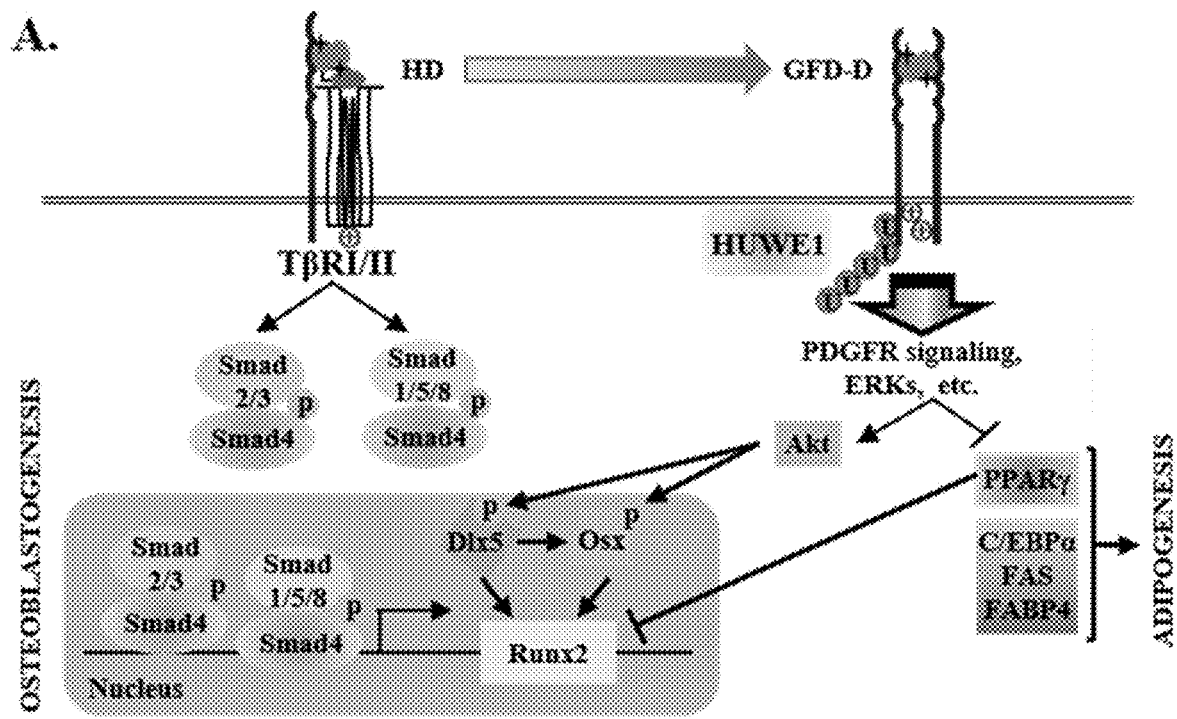
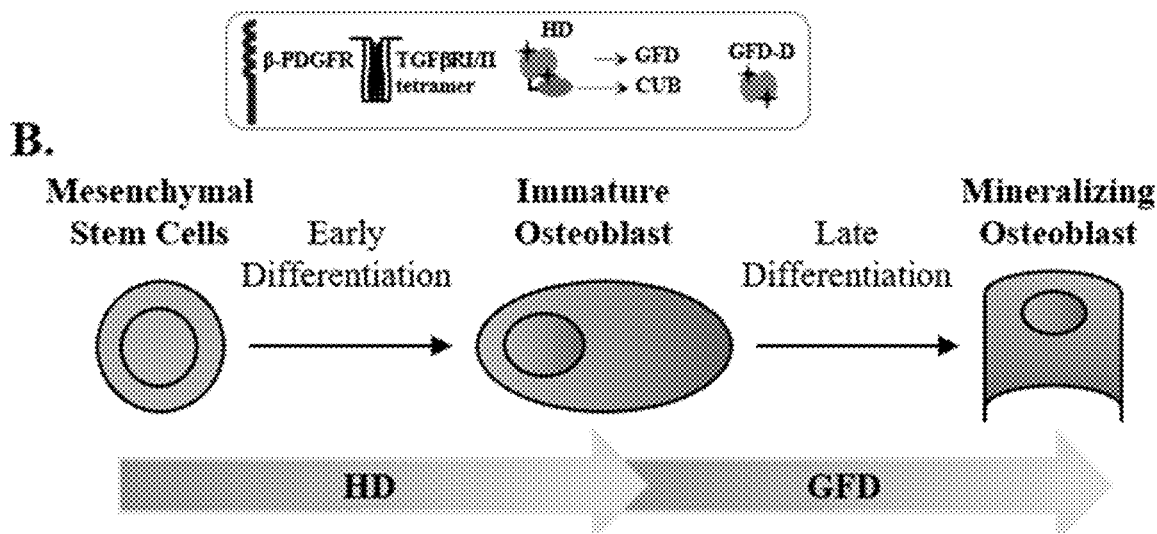
FIG. 9B

```
SEQ ID NO:9   PDGFD   DETIQVKGNGYVQSPRFPNSYPRNLLWRLHSQENTRIQ-LVTDNQFGLEEAEND TR      59
SEQ ID NO:10  BMP1    QPDMN-KDAGQIQSPNYPDDYRPSKQWRITYSGPHVG-LTFQA---FEIERHD SK      55
SEQ ID NO:11  NRP1    DTIKIESPGYLTSPGYPHSYHPSEQWLIQAPDFYQRIMINFNF----HFDLEDRDS X    57
SEQ ID NO:12  SCUBE3  GELG-EFTGYIESPNYPGNYPAGVPQWNINPPFKRKIL-IVVFE----IPLPSEDPP P   55

SEQ ID NO:9   PDGFD   YDFVEVEDISETSTIIRGRHRKEVPPRIKSRTNQIKITFKSDDYFVAKPGFKITY-       116
SEQ ID NO:10  BMP1    YDYLEVRDGPTEESALIGHNFYEK-PEDVKSSNRLWMKFVS-DGSINKAGFAANF-       110
SEQ ID NO:11  NRP1    YDYVEVFDGENENGHFRGKFIA-PPPVVSGPFLFIKFVS-DYETHGAGFSIRYE         113
SEQ ID NO:12  SCUBE3  -DVLVMRKNISPSSITTYEPFYERPIAPTARSRKWINFKT-SEANSARGPQIPY-        110
```

FIG. 10

```
                      SEQUENCE LISTING

<160> NUMBER OF SEQ ID NOS: 12

<210> SEQ ID NO 1
<211> LENGTH: 370
<212> TYPE: PRT
<213> ORGANISM: Homo sapiens

<400> SEQUENCE: 1

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
                20                  25                  30

Leu Arg Asn Ala Asn Leu Arg Arg Asp Glu Ser Asn His Leu Thr Asp
            35                  40                  45

Leu Tyr Arg Arg Asp Glu Thr Ile Gln Val Lys Gly Asn Gly Tyr Val
        50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
        210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285
```

Asn Val Val Phe Phe Pro Arg Cys Leu Leu Val Gln Arg Cys Gly Gly
            290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 2
<211> LENGTH: 1110
<212> TYPE: DNA
<213> ORGANISM: Homo sapiens

<400> SEQUENCE: 2
atgcaccggc tcatctttgt ctacactcta atctgcgcaa acttttgcag ctgtcgggac      60
acttctgcaa ccccgcagag cgcatccatc aaagctttgc gcaacgccaa cctcaggcga     120
gatgagagca atcacctcac agacttgtac cgaagagatg agaccatcca ggtgaaagga     180
aacggctacg tgcagagtcc tagattcccg aacagctacc ccaggaacct gctcctgaca     240
tggcggcttc actctcagga gaatacacgg atacagctag tgtttgacaa tcagtttgga     300
ttagaggaag cagaaaatga tatctgtagg tatgattttg tggaagttga agatatatcc     360
gaaaccagta ccattattag aggacgatgg tgtggacaca aggaagttcc tccaaggata     420
aaatcaagaa cgaaccaaat taaaatcaca ttcaagtccg atgactactt tgtggctaaa     480
cctggattca agatttatta ttctttgctg aagatttcc aacccgcagc agcttcagag     540
accaactggg aatctgtcac aagctctatt tcaggggtat cctataactc tccatcagta     600
acggatccca ctctgattgc ggatgctctg acaaaaaaa ttgcagaatt tgatacagtg     660
gaagatctgc tcaagtactt caatccagag tcatggcaag aagatcttga aatatgtat     720 ctggacaccc ctcggtatcg aggcaggtca taccatgacc ggaagtcaaa agttgacctg     780
gataggctca atgatgatgc caagcgttac agttgcactc ccaggaatta ctcggtcaat     840
ataagagaag agctgaagtt ggccaatgtg gtcttctttc acgttgcct cctcgtgcag     900 cgctgtggag gaaattgtgg ctgtggaact gtcaactgga ggtcctgcac atgcaattca     960
gggaaaaccg tgaaaaagta tcatgaggta ttacagtttg agcctggcca tcaagagg     1020 aggggtagag ctaagaccat ggctctagtt gacatccagt tggatcacca tgaacgatgt    1080
gattgtatct gcagctcaag accacctcga                                      1110

<210> SEQ ID NO 3
<211> LENGTH: 136
<212> TYPE: PRT
<213> ORGANISM: Homo sapiens

<400> SEQUENCE: 3

Asp Leu Glu Asn Met Tyr Leu Asp Thr Pro Arg Tyr Arg Gly Arg Ser
1               5                   10                  15

Tyr His Asp Arg Lys Ser Lys Val Asp Leu Asp Arg Leu Asn Asp Asp
            20                  25                  30

Ala Lys Arg Tyr Ser Cys Thr Pro Arg Asn Tyr Ser Val Asn Ile Arg
            35                  40                  45

Glu Glu Leu Lys Leu Ala Asn Val Val Phe Pro Arg Cys Leu Leu
 50                  55                  60

Val Gln Arg Cys Gly Gly Asn Cys Gly Cys Gly Thr Val Asn Trp Arg
 65                  70                  75                  80

Ser Cys Thr Cys Asn Ser Gly Lys Thr Val Lys Lys Tyr His Glu Val
                 85                  90                  95

Leu Gln Phe Glu Pro Gly His Ile Lys Arg Arg Gly Arg Ala Lys Thr
            100                 105                 110

Met Ala Leu Val Asp Ile Gln Leu Asp His His Glu Arg Cys Asp Cys
            115                 120                 125

Ile Cys Ser Ser Arg Pro Pro Arg
            130                 135

<210> SEQ ID NO 4
<211> LENGTH: 408
<212> TYPE: DNA
<213> ORGANISM: Homo sapiens

<400> SEQUENCE: 4
gatcttgaga atatgtatct ggacacccct cggtatcgag gcaggtcata ccatgaccgg      60
aagtcaaaag ttgacctgga taggctcaat gatgatgcca agcgttacag ttgcactccc     120
aggaattact cggtcaatat aagagaagag ctgaagttgg ccaatgtggt cttctttcca     180
cgttgcctcc tcgtgcagcg ctgtggagga aattgtggct gtggaactgt caactggagg     240
tcctgcacat gcaattcagg gaaaaccgtg aaaaagtatc atgaggtatt acagtttgag     300
cctggccaca tcaagaggag gggtagagct aagaccatgg ctctagttga catccagttg     360
gatcaccatg aacgatgtga ttgtatctgc agctcaagac cacctcga                 408

<210> SEQ ID NO 5
<211> LENGTH: 370
<212> TYPE: PRT
<213> ORGANISM: Artificial Sequence
<220> FEATURE:
<223> OTHER INFORMATION: Mutated variant of PDGF D of SEQ ID NO:1
      including R247A and R249A

<400> SEQUENCE: 5

Met His Arg Leu Ile Phe Val Tyr Thr Leu Ile Cys Ala Asn Phe Cys
  1               5                  10                  15

Ser Cys Arg Asp Thr Ser Ala Thr Pro Gln Ser Ala Ser Ile Lys Ala
                 20                  25                  30

Leu Arg Asn Ala Asn Leu Arg Arg Asp Glu Ser Asn His Leu Thr Asp
             35                  40                  45

Leu Tyr Arg Arg Asp Glu Thr Ile Gln Val Lys Gly Asn Gly Tyr Val
 50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
            115                 120                 125

```
Arg Trp Cys Gly His Lys Glu Val Pro Pro Arg Ile Lys Ser Arg Thr
            130                 135                 140
Asn Gln Ile Lys Ile Thr Phe Lys Ser Asp Asp Tyr Phe Val Ala Lys
145                 150                 155                 160
Pro Gly Phe Lys Ile Tyr Tyr Ser Leu Leu Glu Asp Phe Gln Pro Ala
                165                 170                 175
Ala Ala Ser Glu Thr Asn Trp Glu Ser Val Thr Ser Ser Ile Ser Gly
            180                 185                 190
Val Ser Tyr Asn Ser Pro Ser Val Thr Asp Pro Thr Leu Ile Ala Asp
        195                 200                 205
Ala Leu Asp Lys Lys Ile Ala Glu Phe Asp Thr Val Glu Asp Leu Leu
    210                 215                 220
Lys Tyr Phe Asn Pro Glu Ser Trp Gln Glu Asp Leu Glu Asn Met Tyr
225                 230                 235                 240
Leu Asp Thr Pro Arg Tyr Ala Gly Ala Ser Tyr His Asp Arg Lys Ser
                245                 250                 255
Lys Val Asp Leu Asp Arg Leu Asn Asp Asp Ala Lys Arg Tyr Ser Cys
            260                 265                 270
Thr Pro Arg Asn Tyr Ser Val Asn Ile Arg Glu Glu Leu Lys Leu Ala
        275                 280                 285
Asn Val Val Phe Phe Pro Arg Cys Leu Leu Val Gln Arg Cys Gly Gly
    290                 295                 300
Asn Cys Gly Cys Gly Thr Val Asn Trp Arg Ser Cys Thr Cys Asn Ser
305                 310                 315                 320
Gly Lys Thr Val Lys Lys Tyr His Glu Val Leu Gln Phe Glu Pro Gly
                325                 330                 335
His Ile Lys Arg Arg Gly Arg Ala Lys Thr Met Ala Leu Val Asp Ile
            340                 345                 350
Gln Leu Asp His His Glu Arg Cys Asp Cys Ile Cys Ser Ser Arg Pro
        355                 360                 365
Pro Arg
    370

<210> SEQ ID NO 6
<211> LENGTH: 21
<212> TYPE: PRT
<213> ORGANISM: Artificial Sequence
<220> FEATURE:
<223> OTHER INFORMATION: Ig kappa-chain leader sequence

<400> SEQUENCE: 6

Met Glu Thr Asp Thr Leu Leu Leu Trp Val Leu Leu Leu Trp Val Pro
1               5                   10                  15
Gly Ser Thr Gly Asp
            20

<210> SEQ ID NO 7
<211> LENGTH: 174
<212> TYPE: PRT
<213> ORGANISM: Artificial Sequence
<220> FEATURE:
<223> OTHER INFORMATION: Fusion protein including GFD subunit protein
      and an Ig kappa-chain leader sequence

<400> SEQUENCE: 7

Met Glu Thr Asp Thr Leu Leu Leu Trp Val Leu Leu Leu Trp Val Pro
1               5                   10                  15
```

Gly Ser Thr Gly Asp Ala Ala Gln Pro Ala Arg Arg Ala Val Arg Ser
            20                  25                  30

Leu Val Pro Ser Ser Asp Leu Glu Asn Met Tyr Leu Asp Thr Pro Arg
        35                  40                  45

Tyr Arg Gly Arg Ser Tyr His Asp Arg Lys Ser Lys Val Asp Leu Asp
50                  55                  60

Arg Leu Asn Asp Asp Ala Lys Arg Tyr Ser Cys Thr Pro Arg Asn Tyr
65                  70                  75                  80

Ser Val Asn Ile Arg Glu Glu Leu Lys Leu Ala Asn Val Val Phe Phe
                85                  90                  95

Pro Arg Cys Leu Leu Val Gln Arg Cys Gly Gly Asn Cys Gly Cys Gly
            100                 105                 110

Thr Val Asn Trp Arg Ser Cys Thr Cys Asn Ser Gly Lys Thr Val Lys
        115                 120                 125

Lys Tyr His Glu Val Leu Gln Phe Glu Pro Gly His Ile Lys Arg Arg
130                 135                 140

Gly Arg Ala Lys Thr Met Ala Leu Val Asp Ile Gln Leu Asp His His
145                 150                 155                 160

Glu Arg Cys Asp Cys Ile Cys Ser Ser Arg Pro Pro Arg Ile
                165                 170

<210> SEQ ID NO 8
<211> LENGTH: 525
<212> TYPE: DNA
<213> ORGANISM: Artificial Sequence
<220> FEATURE:
<223> OTHER INFORMATION: Sequence encoding fusion protein including GFD
      subunit protein and an Ig kappa-chain leader sequence

<400> SEQUENCE: 8
atggagacag acacactcct gctatgggta ctgctgctct gggttccagg ttccactggt      60
gacgcggccc agccggccag gcgcgccgta cgaagcttgg taccgagctc ggatcttgag     120
aatatgtatc tggacacccc tcggtatcga ggcaggtcat accatgaccg gaagtcaaaa     180
gttgacctgg ataggctcaa tgatgatgcc aagcgttaca gttgcactcc aggaattac      240 tcggtcaata taagagaaga gctgaagttg gccaatgtgg tcttctttcc acgttgcctc     300
ctcgtgcagc gctgtggagg aaattgtggc tgtggaactg tcaactggag gtcctgcaca     360
tgcaattcag ggaaaaccgt gaaaaagtat catgaggtat tacagtttga gcctggccac     420
atcaagagga ggggtagagc taagaccatg gctctagttg acatccagtt ggatcaccat     480
gaacgatgcg attgtatctg cagctcaaga ccacctcgaa tttga                     525

<210> SEQ ID NO 9
<211> LENGTH: 116
<212> TYPE: PRT
<213> ORGANISM: Homo sapiens

<400> SEQUENCE: 9

Arg Asp Glu Thr Ile Gln Val Lys Gly Asn Gly Tyr Val Gln Ser Pro
1               5                   10                  15

Arg Phe Pro Asn Ser Tyr Pro Arg Asn Leu Ile Leu Thr Trp Arg Leu
            20                  25                  30

His Ser Gln Glu Asn Thr Arg Ile Gln Leu Val Phe Asp Asn Gln Phe
        35                  40                  45

Gly Leu Glu Glu Ala Glu Asn Asp Ile Cys Arg Tyr Asp Phe Val Glu
    50                  55                  60

```
Val Glu Asp Ile Ser Glu Thr Ser Thr Ile Ile Arg Gly Arg Trp Cys
 65                  70                  75                  80

Gly His Lys Glu Val Pro Pro Arg Ile Lys Ser Arg Thr Asn Gln Ile
                 85                  90                  95

Lys Ile Thr Phe Lys Ser Asp Asp Tyr Phe Val Ala Lys Pro Gly Phe
            100                 105                 110

Lys Ile Tyr Tyr
        115

<210> SEQ ID NO 10
<211> LENGTH: 110
<212> TYPE: PRT
<213> ORGANISM: Homo sapiens

<400> SEQUENCE: 10

Cys Gly Gly Asp Met Asn Lys Asp Ala Gly Gln Ile Gln Ser Pro Asn
  1               5                  10                  15

Tyr Pro Asp Asp Tyr Arg Pro Ser Lys Glu Cys Val Trp Arg Ile Thr
             20                  25                  30

Val Ser Glu Gly Phe His Val Gly Leu Thr Phe Gln Ala Phe Glu Ile
         35                  40                  45

Glu Arg His Asp Ser Cys Ala Tyr Asp Tyr Leu Glu Val Arg Asp Gly
 50                  55                  60

Pro Thr Glu Glu Ser Ala Leu Ile Gly His Phe Cys Gly Tyr Glu Lys
 65                  70                  75                  80

Pro Glu Asp Val Lys Ser Ser Asn Arg Leu Trp Met Lys Phe Val
                 85                  90                  95

Ser Asp Gly Ser Ile Asn Lys Ala Gly Phe Ala Ala Asn Phe
            100                 105                 110

<210> SEQ ID NO 11
<211> LENGTH: 113
<212> TYPE: PRT
<213> ORGANISM: Homo sapiens

<400> SEQUENCE: 11

Cys Gly Asp Thr Ile Lys Ile Glu Ser Pro Gly Tyr Leu Thr Ser Pro
  1               5                  10                  15

Gly Tyr Pro His Ser Tyr His Pro Ser Glu Lys Cys Glu Trp Leu Ile
             20                  25                  30

Gln Ala Pro Asp Pro Tyr Gln Arg Ile Met Ile Asn Phe Asn Pro His
         35                  40                  45

Phe Asp Leu Glu Asp Arg Asp Cys Lys Tyr Asp Tyr Val Glu Val Phe
 50                  55                  60

Asp Gly Glu Asn Glu Asn Gly His Phe Arg Gly Lys Phe Cys Gly Lys
 65                  70                  75                  80

Ile Ala Pro Pro Pro Val Val Ser Ser Gly Pro Phe Leu Phe Ile Lys
                 85                  90                  95

Phe Val Ser Asp Tyr Glu Thr His Gly Ala Gly Phe Ser Ile Arg Tyr
            100                 105                 110

Glu

<210> SEQ ID NO 12
<211> LENGTH: 110
<212> TYPE: PRT
<213> ORGANISM: Homo sapiens
```

<400> SEQUENCE: 12

```
Cys Gly Gly Glu Leu Gly Glu Phe Thr Gly Tyr Ile Glu Ser Pro Asn
1               5                   10                  15

Tyr Pro Gly Asn Tyr Pro Ala Gly Val Glu Cys Ile Trp Asn Ile Asn
            20                  25                  30

Pro Pro Pro Lys Arg Lys Ile Leu Ile Val Val Pro Glu Ile Phe Leu
        35                  40                  45

Pro Ser Glu Asp Glu Cys Gly Asp Val Leu Val Met Arg Lys Asn Ser
    50                  55                  60

Ser Pro Ser Ser Ile Thr Thr Tyr Glu Thr Cys Gln Thr Tyr Glu Arg
65                  70                  75                  80

Pro Ile Ala Phe Thr Ala Arg Ser Arg Lys Leu Trp Ile Asn Phe Lys
                85                  90                  95

Thr Ser Glu Ala Asn Ser Ala Arg Gly Phe Gln Ile Pro Tyr
            100                 105                 110
```

COMPOSITIONS AND METHODS RELATING TO BONE REPAIR AND REGENERATION

REFERENCE TO RELATED APPLICATION

This application claims priority to U.S. Patent Application Ser. No. 63/045,473, filed Jun. 29, 2020, the entire content of which is incorporated herein by reference.

GRANT REFERENCE

This invention was made with government support under Grant No. RO1NIH/NCI CA123362, awarded by the National Institutes of Health. The Government has certain rights in the invention.

FIELD OF THE INVENTION

The present disclosure generally relates methods and compositions promoting bone repair and regeneration. According to specific aspects, methods and compositions including recombinant platelet derived growth factor D (PDGF D) hemidimer (HD) including 1) a full-length PDGF D polypeptide and 2) a C-terminal growth factor domain (GFD) of PDGF D, wherein the GFD lacks a CUB domain promoting regulation of bone marrow mesenchymal stem cell (BMSC) differentiation into osteogenic lineage cells.

BACKGROUND OF THE INVENTION

Stromal osteoprogenitor cells derived from stem cells at the skeletal sites are the principal cells that can differentiate into osteoblasts (OBs) and maintain bone mass. OBs synthesize bone matrix proteins and the fully differentiated osteocytes organize throughout the mineralized bone matrix and support the bone structure. Coordinated bone remodeling is critical not only for the maintenance of healthy bones but also for the repair of damaged bones.

Bone formation is regulated by many factors such as growth factors, cytokines, and prostaglandins. Among those, transforming growth factor-β (TGF-β), bone morphogenetic protein (BMP) and platelet-derived growth factor B (PDGF B) are thought to play key roles in stem cell proliferation and differentiation into bone cells.

BMPs are osteoinductive growth factors and the use of BMP-2 and BMP-7 for bone regeneration is currently approved by the US Food and Drug Administration (FDA). While BMP and TGF-β are shown to induce stem cell differentiation and commitment to osteoprogenitor cells, preclinical and clinical studies showed marginal effects on bone regeneration when administered alone and the clinical use of these factors is limited due to the requirement of supraphysiological concentrations for bone formation, as described for example in Rindone, A. N., et al., Adv Healthc Mater, 2019. 8(10): p. e1801565.

The PDGF family is composed of 4 ligands (PDGF A, B, C and D) and 2 transmembrane receptor subunits (α- and β-PDGFR), described in detail in Yu, J., et al. J Biochem Mol Biol, 2003. 36(1): p. 49-59. While the α-PDGFR can be activated by PDGF A, B or C, β-PDGFR is activated by PDGF B or D. Consistent with well-established functions of PDGF as a potent chemoattractant and mitogen for cells of mesenchymal origin, PDGF B mediates osteogenic signals through its induction of osteoprogenitor cell migration to the site of bone regeneration and expansion of osteoprogenitor cells in addition to its role in angiogenesis, critical for bone formation, see for example, Bayer, E. A., et al. Tissue Eng Part A, 2016. 22(21-22): p. 1296-1304; Shah, P., et al. J Oral Implantol, 2014. 40(3): p. 330-40; and Caplan, A. I. and D. Correa, J Orthop Res, 2011. 29(12): p. 1795-803.

While the classical PDGF ligands PDGF A and B are secreted as active homodimers or heterodimers, newly identified PDGF C and D are secreted as latent homodimers containing the N-terminal CUB domain and the C-terminal growth factor domain (GFD), as detailed in Bergsten, E., et al., Nat Cell Biol, 2001. 3(5): p. 512-6; LaRochelle, W. J., et al., Nat Cell Biol, 2001. 3(5): p. 517-21; and Li, X., et al., Nat Cell Biol, 2000. 2(5): p. 302-9.

It has been demonstrated that serine protease-mediated proteolytic removal of the CUB domain is required for the GFD of PDGF C and D to activate its cognate receptor α-PDGFR and β-PDGFR, respectively, see Ustach, C. V. and H. R. Kim, Mol Cell Biol, 2005. 25(14): p. 6279-88; Ustach, C. V., et al., Cancer Res, 2010. 70(23): p. 9631-40; and Hurst, N.J., Jr., et al., Biochem J, 2012. 441(3): p. 909-18.

Although both PDGF B and PDGF D are activators of β-PDGFR, increasing evidence suggests unique functions of PDGF D compared to PDGF B, see Li, H., et al., Oncogene, 2003. 22(10): p. 1501-10; Ehnman, M., et al., Oncogene, 2009. 28(4): p. 534-44; Najy, A. J., et al., Mol Cancer Res, 2012. 10(8): p. 1087-97; and Najy, A. J., et al., Am J Physiol Cell Physiol, 2016. 310(4): p. C293-304.

The present disclosure relates to a novel function of PDGF D in the regulation of bone marrow mesenchymal stem cell (BMSC) differentiation into osteogenic lineage cells, involving the PDGF D HD/β-PDGFR/TGFbR/SMADs signaling axis as well as a unique GFD dimer (GFD-D)/β-PDGFR signaling program.

There is a continuing need for compositions and methods for promoting bone repair and regeneration.

SUMMARY OF THE INVENTION

Methods of treating a subject in need thereof are provided according to aspects of the present disclosure which include: administering a recombinant platelet derived growth factor D (PDGF D) composition to a mesenchymal stem cell of the subject and/or a progenitor derived therefrom, producing a treated mesenchymal stem cell of the subject and/or a progenitor derived therefrom, thereby stimulating the mesenchymal stem cell and/or a progenitor derived therefrom.

Methods and compositions are provided according to aspects of the present disclosure including recombinant platelet derived growth factor D (PDGF D) hemidimer (HD) including 1) a full-length PDGF D polypeptide and 2) a C-terminal growth factor domain (GFD) of PDGF D, wherein the GFD lacks a CUB domain promoting regulation of bone marrow mesenchymal stem cell (BMSC) differentiation into osteogenic lineage cells.

Methods of treating a subject in need thereof are provided according to aspects of the present disclosure which include: administering a recombinant platelet derived growth factor D (PDGF D) composition to a mesenchymal stem cell of the subject and/or a progenitor derived therefrom, in vivo, in vitro, or ex vivo, producing a treated mesenchymal stem cell of the subject and/or a progenitor derived therefrom, thereby stimulating the mesenchymal stem cell (MSC) and/or a progenitor derived therefrom. Ex vivo and/or in vitro administration of the recombinant PDGF D composition treated MSC or MSC of the subject may be followed by administration of the treated cell to the subject.

Methods of treating a subject in need thereof are provided according to aspects of the present disclosure which include: administering an expression vector encoding a recombinant PDGF D composition to a mesenchymal stem cell of the subject and/or a progenitor derived therefrom, in vivo, in vitro, or ex vivo, producing a treated mesenchymal stem cell of the subject and/or a progenitor derived therefrom which expresses the recombinant PDGF D composition. Cells expressing the recombinant PDGF D composition can be administered to the subject, thereby treating the subject in need thereof.

According to aspects of the present disclosure, the subject is in need of bone repair, bone regeneration, or adipocyte inhibition. According to aspects of the present disclosure, the subject in need of adipocyte inhibition has age-associated bone loss with increased adipogenesis.

According to aspects of the present disclosure, methods of treating a subject in need thereof are provided which further include administering a GFD dimer.

According to aspects of the present disclosure, the PDGF D composition comprises a hemidimer (HD) including 1) a full-length PDGF D polypeptide and 2) a GFD of PDGF D, wherein the GFD lacks a CUB domain.

According to aspects of the present disclosure, the full-length PDGF D polypeptide is wild-type or cleavage resistant (CR).

According to aspects of the present disclosure, the full-length PDGF D comprises an amino acid sequence with at least 85% sequence identity to SEQ ID NO: 1 or SEQ ID NO: 5.

According to aspects of the present disclosure, the GFD comprises an amino acid sequence with at least 85% sequence identity to SEQ ID NO: 3 or SEQ ID NO: 7, and optionally includes a mutation in any one, two, or all three of $R^{340}$, $R^{341}$ and $R^{343}$.

According to aspects of the present disclosure, the HD is a wild-type HD or CR-HD.

According to aspects of the present disclosure, the PDGF D hemidimer is administered by introducing a polynucleotide encoding PDGF D full length subunit and a polynucleotide encoding PDGF D GFD to the mesenchymal stem cell and/or progenitor derived therefrom, wherein the mesenchymal stem cell and/or progenitor derived therefrom translates the polynucleotide or produces a transcript thereof, whereby the PDGF D hemidimer is produced in the mesenchymal stem cell and/or progenitor derived therefrom.

According to aspects of the present disclosure, the GFD dimer is administered by introducing a polynucleotide encoding a PDGF D GFD to the mesenchymal stem cell and/or progenitor derived therefrom, wherein the cell translates the polynucleotide and/or produces a transcript thereof, whereby the GFD dimer is produced in the mesenchymal stem cell and/or progenitor derived therefrom.

According to aspects of the present disclosure, the mesenchymal stem cell and/or the progenitor derived therefrom is in vitro or in vivo.

According to aspects of the present disclosure, the mesenchymal stem cell and/or the progenitor derived therefrom is in vitro and further comprising administering the treated mesenchymal stem cell of the subject and/or a progenitor derived therefrom to the subject.

According to aspects of the present disclosure, administering the treated mesenchymal stem cell of the subject and/or a progenitor derived therefrom to the subject comprises administration at a site of injury or disease.

Compositions are provided according to aspects of the present disclosure which include a recombinant polypeptide with at least 85% identity to the amino acid sequence set forth in SEQ ID NO: 5, wherein at least one of positions 247 or 249 is a non-charged amino acid, or wherein both positions 247 and 249 are non-charged amino acids. Compositions are provided according to aspects of the present disclosure which further include a recombinant polypeptide with at least 85% identity to the amino acid sequence set forth in SEQ ID NO: 3 or SEQ ID NO:7, and optionally includes a mutation in any one, two, or all three of $R^{340}$, $R^{341}$ and $R^{343}$.

Isolated nucleic acids are provided according to aspects of the present disclosure which encode the recombinant polypeptide with at least 85% identity to the amino acid sequence set forth in SEQ ID NO: 5, wherein at least one of positions 247 or 249 is a non-charged amino acid, or wherein both positions 247 and 249 are non-charged amino acids. Isolated nucleic acids are provided according to aspects of the present disclosure which encode the recombinant polypeptide with at least 85% identity to the amino acid sequence set forth in SEQ ID NO: 3 or SEQ ID NO:7, and optionally includes a mutation in any one, two, or all three of $R^{340}$, $R^{341}$ and $R^{343}$.

Compositions composition for stimulating bone growth or inhibiting adipocytes are provided according to aspects of the present disclosure which include a recombinant PDGF D wild-type hemidimer or CR-HD, and a recombinant GFD dimer. Compositions composition for stimulating bone growth or inhibiting adipocytes are provided according to aspects of the present disclosure which include a nucleic acid encoding the PDGF D full length subunit polypeptide, and a nucleic acid encoding the GFD subunit polypeptide.

BRIEF DESCRIPTION OF THE DRAWINGS

FIG. 1A shows an immunoblot analysis of recombinant PDGF D (rPDGF D) proteins processed by increasing concentrations of matriptase in nonreducing (top) and reducing (middle) conditions and its activation of β-PDGFR in NIH3T3 cells (bottom 2 panels) FIG. 1B shows schematic diagram of full-length dimer (FL-D), hemidimer (HD) and GFD-D; R247, R249 in the serine protease (such as matriptase) cleavage site in the hinge region. FIGS. 1C-1E PDGF D dimer species (FL-D, HD, and GFD-D) were extracted from a non-reducing SDS-PAGE gel (FIG. 1C), resolved on non-reducing (FIG. 1D) and reducing SDS-PAGE gel (FIG. 1E);

FIG. 2A shows alkaline phosphatase (ALP) activity assay and Alizarin Red S (ARS) staining. FIG. 2B shows hBMSCs were treated with 200 ng/ml BMP-4 or 2 µg/ml concentrated CM from PDGF D expressing LNCaP cells in the presence or absence of 2 µg/ml neutralizing antibody against PDGF D (αD Ab), then ALP activity was determined. FIG. 2C shows immunoblot analysis of PDGF B and PDGF D using indicated CM. FIG. 2D shows the β-PDGFR activation assay in serum-starved NIH3T3 cells or hBMSCs using serum-free (SF) media, or CM from control (Neo), PDGF B- or PDGF D-transfected LNCaP. These data suggest the formation of unique β-PDGFR signaling complex induced by PDGF D in hBMSCs;

FIG. 6A shows serum starved hBMSC were treated with indicated PDGF ligand for 10 minutes. Immunoblot analysis was performed with the indicated antibodies (Abs). FIG. 6B shows the β-PDGFR activation assay in serum starved NIH3T3 upon 10 min treatment with PDGF B or PDGF D GFD-D;

FIG. 8A shows hBMSCs were induced to differentiate into adipocytes using adipogenic media (AD) with and without 1 nM GFD-D for 2 weeks then lipid droplets stained with Oil Red O and quantified. FIG. 8B shows hBMSCs were grown under normal growth (Mes) or adipogenic (AD) conditions in the presence or absence of 1 nM GFD for two weeks. Cell lysates were subjected to immunoblot analysis for adipogenic markers.

FIGS. 9A and 9B show a working model for PDGF D dimer-specific regulation of osteoblastogenic differentiation of BMSC;

FIG. 10 shows alignment of CUB domains. Amino acid sequences of CUB domain of PDGF D (SEQ ID NO:9), BMP1 (SEQ ID NO:10), NRP1 (SEQ ID NO:11), and SCUBE3 (SEQ ID NO:12) were aligned. The 4 consensus cysteines are boxed.

DETAILED DESCRIPTION OF THE INVENTION

Figure 1A:
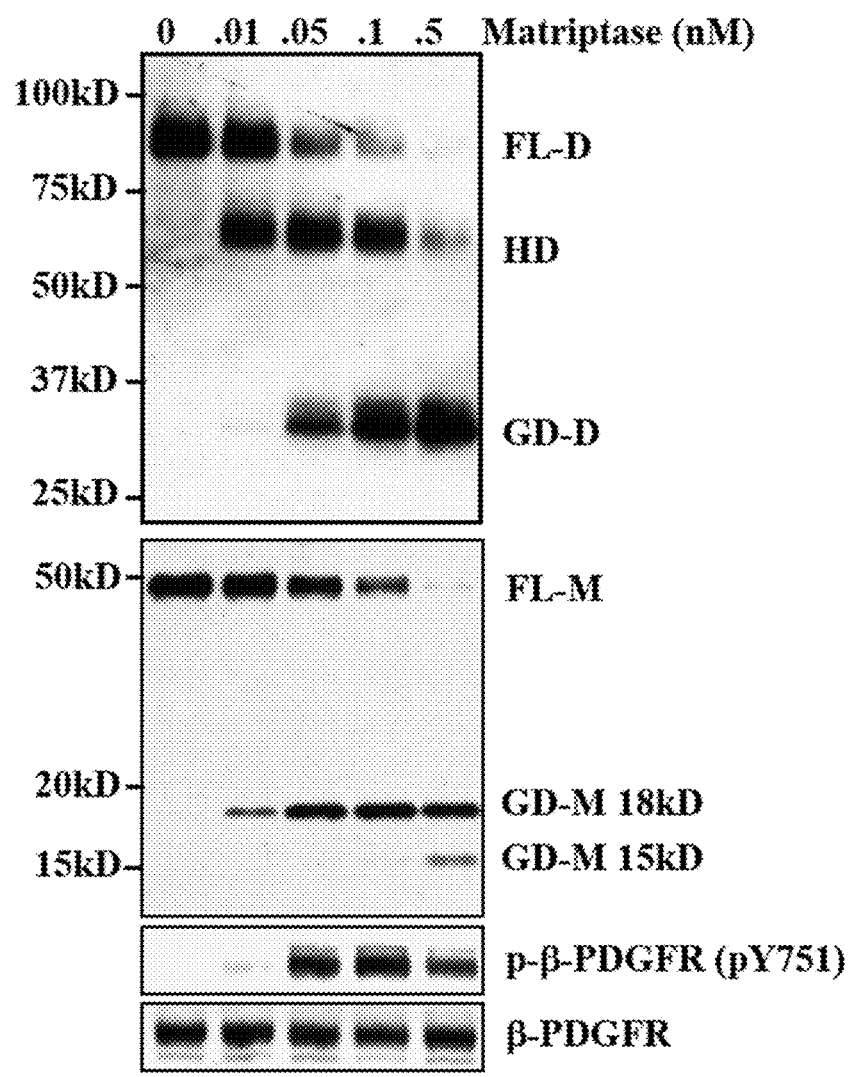
FIGS. 1A–1E show characterization of PDGF D dimer species.

Scientific and technical terms used herein are intended to have the meanings commonly understood by those of ordinary skill in the art. Such terms are found defined and used in context in various standard references illustratively including M. R. Green and J. Sambrook, Molecular Cloning: A Laboratory Manual, Cold Spring Harbor Laboratory Press; 4th Ed., 2012; F. M. Ausubel, Ed., Short Protocols in Molecular Biology, Current Protocols; 5th Ed., 2002; B. Alberts et al., Molecular Biology of the Cell, 4th Ed., Garland, 2002; CRISPR/Cas: A Laboratory Manual, Doudna and Mali (eds), Cold Spring Harbor Laboratory Press, Cold Spring Harbor, NY, USA, 2016; D. L. Nelson and M. M. Cox, Lehninger Principles of Biochemistry, 4th Ed., W. H. Freeman & Company, 2004; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005; L. V. Allen, Jr. et al., Ansel□s Pharmaceutical Dosage Forms and Drug Delivery Systems, 8th Ed., Philadelphia, PA: Lippincott, Williams & Wilkins, 2004; and L. Brunton et al., Goodman & Gilman□s The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The present disclosure relates to methods and isolated protein compositions for stimulating bone repair and regeneration.

Compositions disclosed herein have been identified to stimulate both the production of osteoprogenitor cells and the differentiation of mesenchymal stem cells or derivatives therefrom to mature osteoblasts. Methods for stimulation of production of osteoprogenitor cells and differentiation of mesenchymal stem cells or derivatives thereof to mature osteoblasts are provided according to the present disclosure for promoting bone repair and regeneration.

Compositions of the present disclosure concern recombinant and/or isolated modified platelet derived growth factor D (PDGF D) proteins or fragments thereof. PDFG D includes two domains, a N-terminal CUB domain and a C-terminal growth factor domain (GFD). Endogenously, a serine protease will cleave the CUB domain off to leave a GFD.

PDGF D is also known to dimerize. Endogenously, a full length PDGF D subunit will form a homodimer with another PDGF D subunit through disulfide bonds between the corresponding GFD sub-domains. The protease site on PDGF D and the inclination to dimerize provide three potential combinations of dimers: full length PDGF D dimer (FL-D), GFD dimer (GFD-D) and a hemidimer (HD) which includes one full-length PDGF D and one GFD subunit. The terms □ dimer□ and □ hemidimer□ both refer to a polypeptide which includes two linked subunits.

According to aspects of the present disclosure, PDGF D hemidimer compositions are used to stimulate the differentiation of mesenchymal stem cells or derivatives therefrom to osteogenic cells. As such, PDGF D hemidimer compositions are administered to mesenchymal stem cells or progenitor derivatives therefrom according to aspects of the present disclosure.

According to aspects of the present disclosure, PDGF D hemidimer compositions are used in combination with GFD-D dimer compositions to stimulate the differentiation of mesenchymal stem cells or derivatives therefrom to mature osteoblasts. As such, PDGF D hemidimer compositions in combination with GFD-D dimer compositions are administered to mesenchymal stem cells or progenitor derivatives therefrom according to aspects of the present disclosure.

The term □ PDGF D hemidimer□ as used herein refers to a polypeptide having two subunits, namely, one full-length PDGF D subunit and one GFD, wherein the full-length PDGF D submit and the GFD are linked. According to aspects, the full-length PDGF D submit and the GFD are linked via interchain disulfide bond.

SEQ ID NO:1 is a full length PDGF D □ wild-type□ subunit protein of a PDGF D hemidimer.

GenBank: NP_079484.1 [*Homo sapiens*] Full length PDGF D subunit protein (370aa)

(SEQ ID NO: 1)
MHRLIFVYTLICANFCSCRDTSATPQSASIKALRN

ANLRRDESNHLTDLYRRDETIQVKGNGYVQSPRFP

NSYPRNLLLTWRLHSQENTRIQLVFDNQFGLEEAE

NDICRYDFVEVEDISETSTIIRGRWCGHKEVPPRI

KSRTNQIKITFKSDDYFVAKPGFKIYYSLLEDFQP

AAASETNWESVTSSISGVSYNSPSVTDPTLIADAL

DKKIAEFDTVEDLLKYFNPESWQEDLENMYLDTPR

YRGRSYHDRKSKVDLDRLNDDAKRYSCTPRNYSVN

1REELKLANVVFFPRCLLVQRCGGNCGCGTVNWRS

CTCNSGKTVKKYHEVLQFEPGHIKRRGRAKTMALV

DIQLDHHERCDCICSSRPPR

SEQ ID NO:2 is a nucleic acid sequence encoding the full length PDGF D subunit protein of SEQ ID NO:1 of a PDGF D hemidimer.

GenBank: NM_025208.5 [*Homo sapiens*], Full length PDGF D subunit protein of SEQ ID NO:1 is encoded by SEQ ID NO:2 (1110b).

(SEQ ID NO: 2)
atgcaccggctcatctttgtctacactctaatctg cgcaaacttttgcagctgtcgggacacttctgcaa ccccgcagagcgcatccatcaaagctttgcgcaac gccaacctcaggcgagatgagagcaatcacctcac agacttgtaccgaagagatgagaccatccaggtga aaggaaacggctacgtgcagagtcctagattccg aacagctaccccaggaacctgctcctgacatggcg gcttcactctcaggagaatacacggatacagctag tgtttgacaatcagtttggattagaggaagcagaa aatgatatctgtaggtatgattttgtggaagttga agatatatccgaaaccagtaccattattagaggac gatggtgtggacacaaggaagttcctccaaggata aaatcaagaacgaaccaaattaaaatcacattcaa gtccgatgactactttgtggctaaacctggattca agatttattattctttgctggaagatttccaaccc gcagcagcttcagagaccaactgggaatctgtcac aagctctatttcaggggtatcctataactctccat cagtaacggatcccactctgattgcggatgctctg gacaaaaaattgcagaatttgatacagtggaaga tctgctcaagtacttcaatccagagtcatggcaag aagatcttgagaatatgtatctggacacccctcgg tatcgaggcaggtcataccatgaccggaagtcaaa -continued agttgacctggataggctcaatgatgatgccaagc gttacagttgcactcccaggaattactcggtcaat ataagagaagagctgaagttggccaatgtggtctt cttccacgttgcctcctcgtgcagcgctgtggag gaaattgtggctgtggaactgtcaactggaggtcc tgcacatgcaattcagggaaaaccgtgaaaaagta tcatgaggtattacagtttgagcctggccacatca agaggaggggtagagctaagaccatggctctagtt gacatccagttggatcaccatgaacgatgtgattg tatctgcagctcaagaccacctcga SEQ ID NO:3 is a [ wild type] GFD subunit protein of a PDGF D hemidimer or GFD-dimer (D235 [ R370 of SEQ ID NO:1).

(SEQ ID NO: 3)

```
DLENMYLDTPRYRGRSYHDRKSKVDLDRLNDDAKR
YSCTPRNYSVN1REELKLANVVFFPRCLLVQRCGG
NCGCGTVNWRSCTCNSGKTVKKYHEVLQFEPGHIK
RRGRAKTMALVDIQLDHHERCDCICSSRPPR
```

SEQ ID NO:4 is a nucleic acid sequence encoding a GFD subunit protein of SEQ ID NO:3 of a PDGF D hemidimer or GFD-dimer.

(SEQ ID NO: 4)

```
gatcttgagaatatgtatctggacacccctcggta
tcgaggcaggtcataccatgaccggaagtcaaaag
ttgacctggataggctcaatgatgatgccaagcgt
tacagttgcactcccaggaattactcggtcaatat
aagagaagagctgaagttggccaatgtggtcttct
ttccacgttgcctcctcgtgcagcgctgtggagga
aattgtggctgtggaactgtcaactggaggtcctg
cacatgcaattcagggaaaaccgtgaaaaagtatc
atgaggtattacagtttgagcctggccacatcaag
aggaggggtagagctaagaccatggctctagttga
catccagttggatcaccatgaacgatgtgattgta
tctgcagctcaagaccacctcga
```

In some instances, the PDGF D is a mutated variant, such that the protease cleavage site is changed to be inoperable. Particular mutations can include changing arginine residues at positions 247 and 249 of full length PDGF D. Mutations of either or both of the arginine residues at positions 247 and 249 to different amino acids can affect the ability of serine protease to cleave the protein. According to aspects of the present disclosure, mutations of R247 and/or R249 to a non-charged amino acid provide a protease cleavage resistant (CR) full length PDGF D (CR-FL PDGF D). According to aspects of the present disclosure, one or both of R247 and/or R249 are mutated to an amino acid independently selected from glycine, alanine, valine, leucine, and isoleucine, providing a CR-FL PDGF D. According to aspects of the present disclosure, one or both of R247 and/or R249 are mutated to alanine, providing a CR-FL PDGF D.

An exemplary amino acid sequence for a serine protease cleavage-resistant PDGF D is set forth in SEQ ID NO: 5 (mutations of R247 and/or R249 to alanine are in bold and underlined):

(SEQ ID NO: 5)
MHRLIFVYTLICANFCSCRDTSATPQSASIKALRN

ANLRRDESNHLTDLYRRDETIQVKGNGYVQSPRFP

NSYPRNLLLTWRLHSQENTRIQLVFDNQFGLEEAE

NDICRYDFVEVEDISETSTIIRGRWCGHKEVPPRI

KSRTNQIKITFKSDDYFVAKPGFKIYYSLLEDFQP

AAASETNWESVTSSISGVSYNSPSVTDPTLIADAL

DKKIAEFDTVEDLLKYFNPESWQEDLENMYLDTPR

YAGASYHDRKSKVDLDRLNDDAKRYSCTPRNYSVN

IREELKLANVVFFPRCLLVQRCGGNCGCGTVNWRS

CTCNSGKTVKKYHEVLQFEPGHIKRRGRAKTMALV

DIQLDHHERCDCICSSRPPR

The cleavage-resistant (CR) PDGF D can be part of a homodimer (CR-FL D or CR-FL PDGF D) or a hemidimer (HD) with a GFD (CR-HD).

According to aspects of the present disclosure, when PDGF D hemidimer is administered without GFD-D, the PDGF D hemidimer is not cleavage-resistant.

It should be also noted that in some instances, both mutations of the arginines at positions 247 and 249 of full length PDGF D may not be desired. For example, one mutation but not both mutations of the arginines at positions 247 and 249 of full length PDGF D may slow cleavage rather than prevent cleavage, such as A247, R249 or R247, A249 mutations of full length PDGF D, increasing the stability of HD but retaining the ability to generate GFD-D.

The $R^{340}R^{341}GR^{343}A$ motif within the loop III of GFD has been identified as a critical structural element for its binding with β-PDGFR as described in Huang, W. et al., J Biol Chem, 2015. 290(14): p. 9162-70. Thus, according to aspects of the present disclosure, a full-length PDGF D subunit and a GFD of the hemidimer or of a GFD dimer, retain the $R^{340}R^{341}GR^{343}A$ motif within the loop III of GFD.

According to aspects of the present disclosure, a full-length PDGF D subunit and a GFD of the hemidimer or of a GFD dimer, include a variant of the $R^{340}R^{341}GR^{343}A$ motif within the loop III of GFD, such as a variant in which any one, two, or all three of $R^{340}R^{341}$ and $R^{343}$ in the $R^{340}R^{341}GR^{343}A$ motif are mutated to a non-charged amino acid. According to aspects of the present disclosure, any one, two, or all three of $R^{340}R^{341}$ and $R^{343}$ in the $R^{340}R^{341}GR^{343}A$ motif are mutated to an amino acid independently selected from glycine, alanine, valine, leucine, and isoleucine. According to aspects of the present disclosure, any one, two, or all three of $R^{340}R^{341}$ and $R^{343}$ in the $R^{340}R^{341}GR^{343}A$ motif are mutated to be alanine.

Figures 2A, 2B:
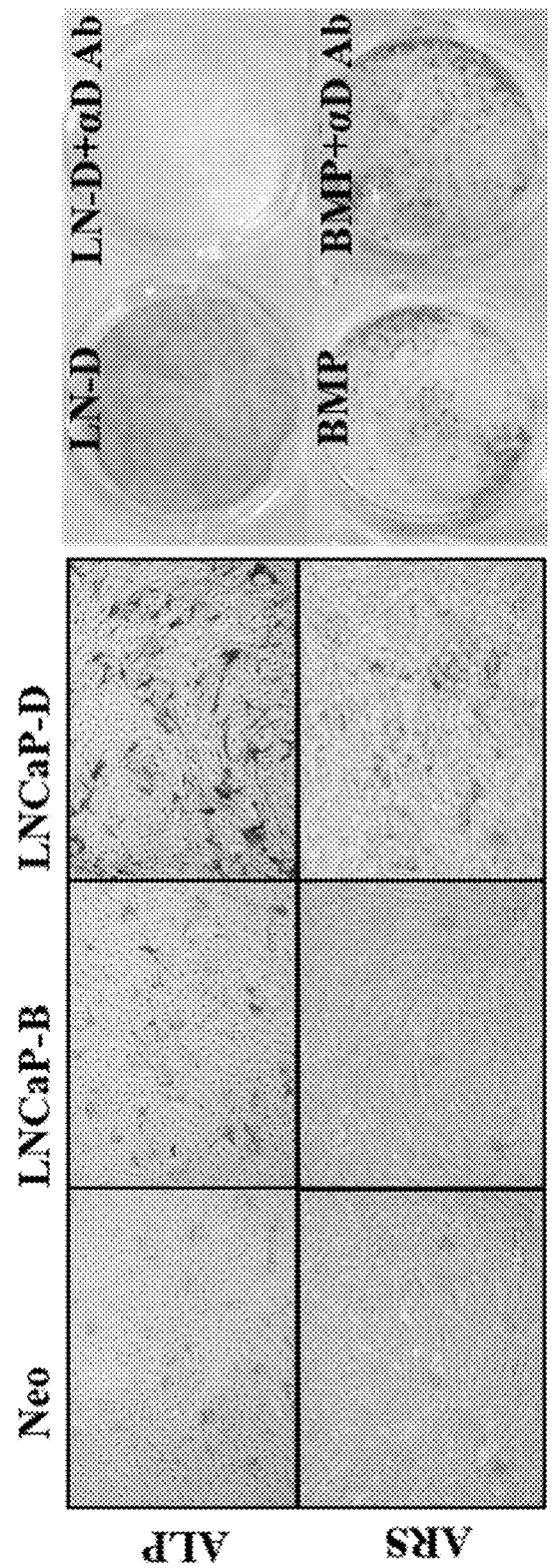
FIGS. 2A-2D show PDGF D induces osteoblastic differentiation. hBMSCs were treated with equal micrograms of LNCaP-derived conditioned medium in osteoblast differentiation medium containing 50 µg/ml ascorbic acid, 10 mM β-glycerolphosphate, 100 nM dexamethasone.
Figures 2C, 2D:
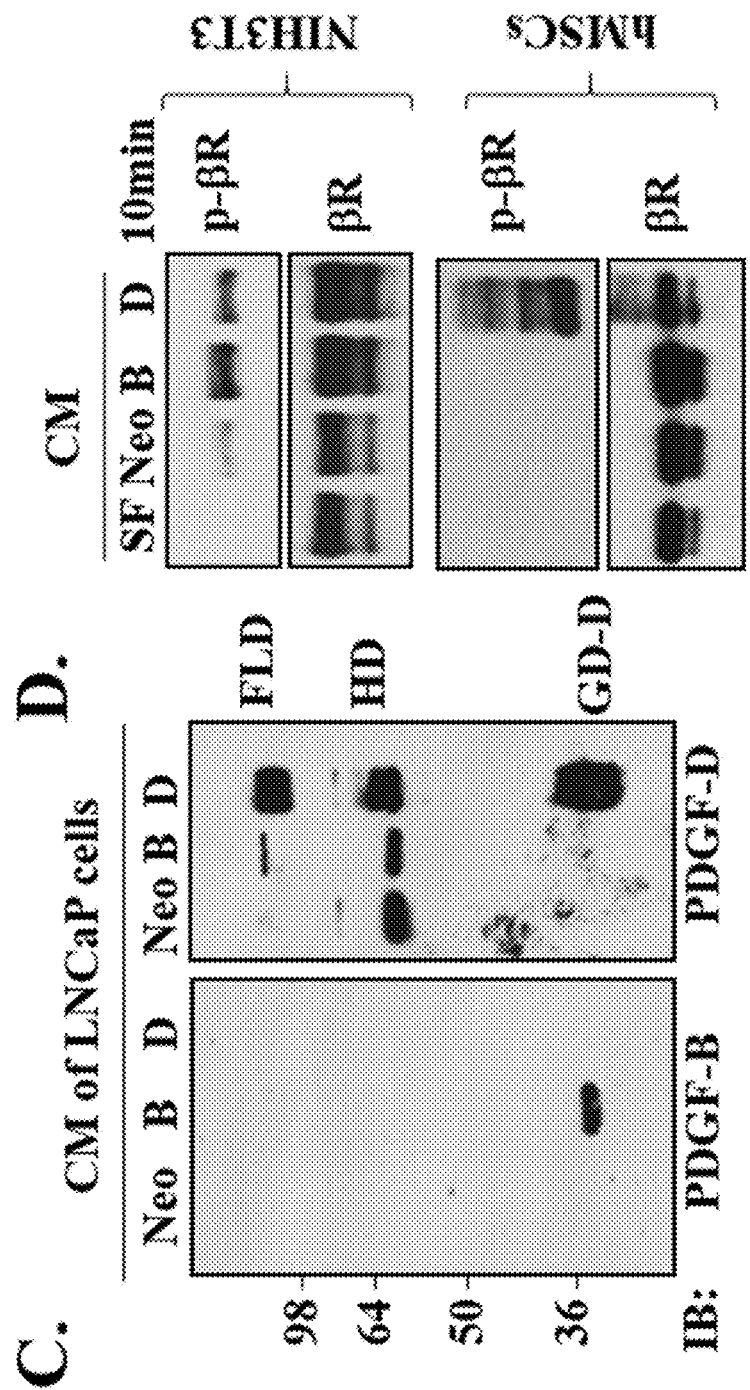

There are eight conserved cysteine residues in PDGFs which form three intrachain disulfide bonds and two interchain disulfide bonds, as depicted in FIG. 2D in Huang, W. et al., JBC, 290(14):9162-9170, 2015.

Intrachain disulfide bonds are formed by: C1-C6, C3-C7, C5-C8, and two interchain disulfide bonds are formed by: C2 and C4. The growth factor domain in PDGF D is missing the 5th cysteine (see FIG. 2D in Huang, W. et al., JBC, 290(14):9162-9170, 2015), thus likely to form two intra- and two interchain disulfide bonds.

Cysteines in the CUB domain may form an intrachain disulfide bridge believed to be critical for the biological activity of the HD. Thus, variants of the HD according to aspects of the present disclosure maintain cysteine residues at positions $C^{58}$ and $C^{80}$.

The full-length PDGF D subunit and the GFD of the hemidimer or the two GFD submits of the GFD dimer may be linked by any of various linkers according to aspects of the present disclosure. According to further particular aspects of the present disclosure, the full-length PDGF D subunit and the GFD of the hemidimer are linked by at least one disulfide bond. According to still further particular aspects of the present disclosure, the full-length PDGF D subunit and the GFD of the hemidimer are linked by at least one interchain disulfide bond between a cysteine residue of the full-length PDGF D subunit and a cysteine residue of the GFD of the hemidimer. According to particular aspects of the present disclosure, the two GFD subunits of the GFD dimer are linked by at least one disulfide bond. According to particular aspects of the present disclosure, the two GFD subunits of the GFD dimer are linked by at least one interchain disulfide bond between cysteine residues of the two GFD subunits.

A PDGF D hemidimer and/or GFD dimer is obtained by methods such as isolation, synthesis, or recombinant expression of one or more nucleic acids encoding the PDGF D hemidimer and/or GFD dimer.

The term [ nucleic acid[] refers to RNA or DNA molecules having more than one nucleotide in any form including single-stranded, double-stranded, oligonucleotide or polynucleotide. The term [ nucleotide sequence[] refers to the ordering of nucleotides in an oligonucleotide or polynucleotide in a single-stranded form of nucleic acid.

A PDGF D hemidimer and/or GFD dimer included in compositions and methods according to aspects of the present disclosure is isolated, and can be recombinantly produced.

Recombinant expression of a PDGF D hemidimer and/or GFD dimer includes expression of a nucleic acid encoding the protein wherein the nucleic acid is included in an expression construct. The terms [ expressing[] and [ expresses[] refer to transcription of a gene to produce a corresponding mRNA and/or translation of the mRNA to produce the corresponding protein.

A host cell may be transfected or infected with the expression construct encoding the desired protein such that the PDGF D hemidimer and/or GFD dimer is expressed in the cell.

The terms [ expression construct[] and [ expression cassette[] are used herein to refer to a double-stranded recombinant DNA molecule containing a desired nucleic acid coding sequence for PDGF D full-length hemidimer subunit protein and/or GFD subunit protein to be expressed and containing one or more regulatory elements necessary or desirable for the expression of the operably linked coding sequence.

Expression constructs operable to express a desired protein include, for example, in operable linkage: a promoter, a DNA sequence encoding a desired protein and a transcription termination site.

The term regulatory element as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (polyA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The term operably linked as used herein refers to a nucleic acid in functional relationship with a second nucleic acid.

A regulatory element included in an expression cassette is a promoter in particular aspects.

The term promoter is well-known in the art and refers to one or more DNA sequences operably linked to a nucleic acid sequence to be transcribed and which bind an RNA polymerase and allow for initiation of transcription. A promoter is typically positioned upstream (5) of a nucleic acid encoding a peptide or protein to be expressed.

An included promoter can be a constitutive promoter or can provide inducible expression. One of skill in the art is familiar with various well-known promoters and is able to select a promoter suitable for use in expressing a peptide or protein in a particular environment, such as in a specified cell type.

For expression in a yeast host cell, suitable promoters include, but are not limited to, an ADH1 promoter, a PGK1 promoter, an ENO promoter, a PYK1 promoter and the like; or a regulatable promoter such as a GAL1 promoter, a GAL 10 promoter, an ADH2 promoter, a PH05 promoter, a CUP1 promoter, a GAL7 promoter, a MET25 promoter, a MET3 promoter, a CYC1 promoter, a HIS 3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1.

For expression in a prokaryotic host cell include, suitable promoters include, but are not limited to, a bacteriophage T7 RNA polymerase promoter; a trp promoter; a lac operon promoter; a trc promoter; a tac promoter; an araBAD promoter; an ssaG promoter; a pagC promoter; a sigma70 promoter, a dps promoter, an spy promoter, an SPI-2 promoter; an actA promoter, an rps M promoter; a tetracycline promoter, an SP6 promoter, a bacteriophage T3 promoter, a gpt promoter and a bacteriophage lambda P promoter.

Additional suitable bacterial and eukaryotic promoters are well-known, for example as described in Sambrook et al., Molecular Cloning, A Laboratory Manual, 2nd ed. 1989; and 3rd ed., 2001; Kriegler, Gene Transfer and Expression: A Laboratory Manual (1990); and Ausubel et al., Current Protocols in Molecular Biology, 2014.

For expression in an eukaryotic cell, promoters that can be included in an expression construct include, but are not limited to, cytomegalovirus immediate early promoter; herpes simplex virus thymidine kinase promoter; early and late SV40 promoters; a phosphoglycerate kinase (PGK) promoter; a promoter present in long terminal repeats from a retrovirus; and a mouse metallothionein-I promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and the long terminal repeat region of Rous Sarcoma virus (RSV promoter).

In addition to a promoter, one or more enhancer sequences may be included such as, but not limited to, cytomegalovirus (CMV) early enhancer element and an SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA and a PDGF D-pA.

An expression construct may include sequences necessary for amplification in bacterial cells, such as a selection marker (e.g., kanamycin or ampicillin resistance gene) and a replicon. An Sh ble gene can be used to provide resistance to zeocin such that zeocin resistance can be used as a selection marker.

An internal ribosome entry site (IRES) is an optionally included nucleic acid sequence that permits translation initiation at an internal site in an mRNA. IRES are well-known in the art, for example as described in Pelletier, J. et al., Nature, 334:320-325, 1988; Vagner, S. et al., EMBO Rep., 2:893-898, 2001; and Hellen, C. U. et al, Genes Dev. 15:1593-1612, 2001.

In some instances, a sequence may be inserted at or near a terminus of the expressed protein. Such sequences are understood to assist in one or more steps of expression, secretion and/or purification. Illustrative purification tags include 6×His, FLAG, biotin, ubiquitin, SUMO, or other tags known in the art. In some instances, a hexa-histidine tag is fused to the GFD at the C-terminus. Inclusion of an Ig κ-chain leader sequence at or near a terminus of the expressed protein (e.g., from the pSecTag2 vector) allows an expressed protein to be readily secreted.

The term transcription termination site refers to a DNA sequence operable to terminate transcription by an RNA polymerase. A transcription termination site is generally positioned downstream (31) of a nucleic acid encoding a peptide or protein to be expressed.

A leader sequence is optionally included in an expression construct. An included leader sequence is, for example, an Ig κ-chain leader sequence: METDTLLLWVLLLWVPG-STGD (SEQ ID NO: 6.

SEQ ID NO:7 shows a GFD subunit protein of a PDGF D hemidimer or GFD-dimer (D235 R370 of SEQ ID NO:1) and including an Ig κ-chain leader sequence of SEQ ID NO:6 along with additional sequences derived from linkers for cloning convenience.

```
                                          (SEQ ID NO: 7)
    METDTLLLWVLLLWVPGSTGDAAQPARRAVRSLVP

SSDLENMYLDTPRYRGRSYHDRKSKVDLDRLNDDA

KRYSCTPRNYSVNIREELKLANVVFFPRCLLVQRC

GGNCGCGTVNWRSCTCNSGKTVKKYHEVLQFEPGH

IKRRGRAKTMALVDIQLDHHERCDCICSSRPPRI
```

SEQ ID NO:8 shows a nucleic acid sequence encoding a GFD subunit protein of SEQ ID NO:7 of a PDGF D hemidimer or GFD-dimer.

```
                                          (SEQ ID NO: 8)
    ATGGAGACAGACACACTCCTGCTATGGGTACTGCT

GCTCTGGGTTCCAGGTTCCACTGGTGACGCGGCCC
```

```
-continued
AGCCGGCCAGGCGCGCCGTACGAAGCTTGGTACCG

AGCTCGGATCTTGAGAATATGTATCTGGACACCCC

TCGGTATCGAGGCAGGTCATACCATGACCGGAAGT

CAAAAGTTGACCTGGATAGGCTCAATGATGATGCC

AAGCGTTACAGTTGCACTCCCAGGAATTACTCGGT

CAATATAAGAGAAGAGCTGAAGTTGGCCAATGTGG

TCTTCTTTCCACGTTGCCTCCTCGTGCAGCGCTGT

GGAGGAAATTGTGGCTGTGGAACTGTCAACTGGAG

GTCCTGCACATGCAATTCAGGGAAAACCGTGAAAA

AGTATCATGAGGTATTACAGTTTGAGCCTGGCCAC

ATCAAGAGGAGGGGTAGAGCTAAGACCATGGCTCT

AGTTGACATCCAGTTGGATCACCATGAACGATGCG

ATTGTATCTGCAGCTCAAGACCACCTCGAATTTGA
```

Codon optimization of a nucleic acid encoding a desired protein may be used to improve expression in a particular expression system, for example by improving the efficiency of translation. A selected nucleic acid encoding a desired protein may be codon optimized for expression in any designated host cell, prokaryotic or eukaryotic, such as, but not limited to, bacteria, insect cells, yeast, fungus, bird eggs and mammalian cells.

An expressed protein optionally includes an N-terminal element such as a leader sequence and/or N-terminal methionine.

In addition to one or more nucleic acids encoding a desired PDGF D hemidimer, GFD dimer, or subunit of either thereof, one or more nucleic acid sequences encoding additional proteins can be included in an expression vector. For example, a nucleic acid sequence encoding a reporter, including, but not limited to, beta-galactosidase, green fluorescent protein and antibiotic resistance reporters is optionally included. In a further example, a His-tag, GST-tag or MBP-tag is optionally included.

A nucleic acid encoding a PDGF D hemidimer, GFD dimer, or subunit of either thereof, can be cloned into an expression vector for transformation into prokaryotic or eukaryotic cells and expression of the encoded peptides and/or protein(s). As used herein, "expression vectors" are defined as polynucleotides which, when introduced into an appropriate host cell, an expression system, can be transcribed and translated, producing the encoded polypeptide(s).

Expression vectors are known in the art and include plasmids, cosmids, viruses and bacteriophages, for example. Expression vectors can be prokaryotic vectors, insect vectors, or eukaryotic vectors, for example.

For example, an expression construct including, in operable linkage: a promoter, a DNA sequence encoding a desired protein and a transcription termination site, is included in a plasmid, cosmid, virus or bacteriophage expression vector.

Particular vectors are known in the art and one of skill in the art will recognize an appropriate vector for a specific purpose.

Any suitable expression vector/host cell system can be used for expression of a transcription factor for administration to a subject according to aspects of the present disclosure.

Expression of a PDGF D hemidimer protein, GFD dimer protein, or subunit of either thereof, using a recombinant expression vector is accomplished by introduction of the expression vector(s) into an eukaryotic or prokaryotic host cell expression system such as an insect cell, mammalian cell, yeast cell, fungus, bird egg, bacterial cell or any other single or multicellular organism recognized in the art.

Host cells containing the recombinant expression vector(s) are maintained under conditions wherein the desired protein is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

Highly preferred is a vaccinia virus expression system. A vaccinia virus expression system may be used for expression of a nucleotide sequence encoding PDGF D full length, and/or GFD to produce a PDGF D hemidimer protein and/or GFD dimer protein. The vaccinia virus may be replication competent or replication incompetent. Suitable host cells may be used with vaccinia virus expression vector, such as, but not limited to Syrian hamster kidney cell line, BHK21.

Bacterial cells can be used as the host cells to produce a PDGF D hemidimer protein and/or GFD dimer protein. Recombinant protein expression in bacterial cells and purification of the produced protein may be performed using known protocols, such as described in Paulina Balbás, Argelia Lorence ed., 2004, Recombinant Gene Expression: Reviews and Protocols, Humana Press, New Jersey; Peter E. Vaillancourt, 2003, E. Coli Gene Expression Protocols, Springer Science & Business Media.

Optionally, recombinantly produced PDGF D hemidimer proteins and/or GFD dimer proteins and/or one or more subunits of either thereof are purified to remove endotoxin when an endotoxin producing host cell type is used. For example, an additional washing step can be added during protein purification stage using 10 column volume of 0.2% of Triton™ X114 nonionic detergent to remove endotoxin from bacterially expressed recombinant a PDGF D hemidimer protein and/or GFD dimer protein and/or one or more subunits of either thereof.

Alternatively, in order to produce recombinant PDGF D hemidimer proteins and/or GFD dimer proteins and/or one or more subunits of either thereof which do not trigger endotoxic response in human cells, a genetically modified bacterial strain, ClearColi™ BL21(DE3) can be used as host cells such that no endotoxin removal is required.

For expression in a host cell, any of the well-known procedures for introducing recombinant nucleic acids into host cells may be used, such as infection, calcium phosphate transfection, polybrene, protoplast fusion, electroporation, sonoporation, liposomes and microinjection, examples of which are described in Sambrook et al., Molecular Cloning: A Laboratory Manual, Cold Spring Harbor Laboratory Press, 2001; and Ausubel, F. et al., (Eds.), Current Protocols in Molecular Biology, 2014.

A cell free expression system is optionally used to express a PDGF D hemidimer protein and/or GFD dimer protein and/or one or more subunits of either thereof, such as described in Ausubel, F. et al., (Eds.), Current Protocols in Molecular Biology, 2014.

PDGF D full length hemidimer subunit protein shown herein as SEQ ID NO:1 and GFD subunit protein shown herein as SEQ ID NO:3, and variants of either thereof, can be used in methods according to aspects described herein.

As used herein, the term "variant" refers to a variation of a nucleic acid sequence encoding PDGF D full length hemidimer subunit protein or GFD subunit protein or a variation of a PDGF D full length hemidimer subunit protein or GFD subunit protein in which one or more nucleotides or amino acid residues have been modified by nucleotide or amino acid substitution, addition, or deletion while retaining the function of the PDGF D full length hemidimer subunit encoding nucleic acid sequence or protein or GFD subunit encoding nucleic acid sequence or protein. Variants of a PDGF D full length hemidimer subunit encoding nucleic acid sequence or protein or GFD subunit encoding nucleic acid sequence or protein described herein are characterized by conserved functional properties compared to a reference nucleic acid sequence or protein.

Mutations can be introduced using standard molecular biology techniques, such as chemical synthesis, site-directed mutagenesis and PCR-mediated mutagenesis.

One of skill in the art will recognize that one or more amino acid mutations can be introduced without altering the functional properties of a PDGF D hemidimer or GFD dimer protein. For example, one or more amino acid substitutions, additions, or deletions can be made without altering the functional properties of a PDGF D hemidimer or GFD dimer protein.

Biological activity of a PDGF D hemidimer or GFD dimer protein variant is readily determined by one of skill in the art, for instance using any of the functional assays described herein or other functional assays known in the art.

Variants of a PDGF D hemidimer or GFD dimer protein described herein are characterized by conserved functional properties compared to the corresponding PDGF D hemidimer or GFD dimer protein and have 75%, 80%, 85%, 90%, 95%, 96%, 97%, 98%, 99% or greater identity to the amino acid sequence of a reference PDGF D hemidimer or GFD dimer protein.

When comparing a reference PDGF D hemidimer or GFD dimer protein to a variant, amino acid similarity may be considered in addition to identity of amino acids at corresponding positions in an amino acid sequence. [] Amino acid similarity[] refers to amino acid identity and conservative amino acid substitutions in a putative homologue compared to the corresponding amino acid positions in a reference protein.

Conservative amino acid substitutions can be made in reference proteins to produce variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group.

Amino acids may also be described in terms of relative size, alanine, cysteine, aspartate, glycine, asparagine, proline, threonine, serine, valine, all typically considered to be small.

Exemplary substitutions that take various of the foregoing characteristics into consideration are well known and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present disclosure. BLAST protein searches are performed with the XBLAST program parameters set, e.g., to score 50, word length=3 to obtain amino acid sequences homologous to a protein molecule of the present disclosure. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleic acid or amino acid mutations can be introduced without altering the functional properties of a given nucleic acid or protein, respectively.

As noted, in PDGF D hemidimer, full length subunit protein shown herein as SEQ ID NO:1 is encoded by the nucleic acid sequence of SEQ ID NO:2 and GFD subunit protein shown herein as SEQ ID NO:3 is encoded by the nucleic acid sequence of SEQ ID NO:4. It is appreciated that due to the degenerate nature of the genetic code, alternate nucleic acid sequences encode a particular protein, and that such alternate nucleic acids may be expressed to produce the desired protein.

Nucleic acid variants can be identified by sequence comparison to determine a percent identity and/or homology. Nucleic acid variants can also be identified by their ability to hybridize under specified hybridization conditions to a complementary reference sequence, e.g., SEQ ID NO: 2 or SEQ ID NO:4.

The term [] complementary[] refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a [] percent complementarity[] to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3[]-TCGA-5[] is 100% complementary to the nucleotide sequence 5[]-AGCT-3[]. Further, the nucleotide sequence 3[]-TCGA-5[] is 100% complementary to a region of the nucleotide sequence 5[]-TTAGCTGG-3[].

The terms [] hybridization[] and [] hybridizes[] refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term [] stringency of hybridization conditions[] refers to conditions of temperature, ionic strength, and composition of a hybridization medium with respect to particular common additives such as formamide and Denhardt[]s solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms [] specific hybridization[] and [] specifically hybridizes[] refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL® blocking agent/0.02% polyvinylpyrrolidone.

A PDGF D hemidimer protein and/or GFD dimer protein is an isolated protein according to aspects of the present disclosure. The term [] isolated protein[] indicates that the protein has been separated from biological materials, such as cells, cellular debris and other proteins, which may be present in the system in which the protein is produced. The term [] isolated protein[] may, but does not necessarily, indicate that the protein is purified. Purified protein included in methods and compositions of the present disclosure contains least about 1 [] 100% of the mass, by weight, such as about 25%, 50%, 75%, 85%, 95%, 99% or greater than about 99% of the mass, by weight, of the protein included. The [] purified[] or [] isolated[] composition substantially retains its biological activity.

Transgenic Non-Human Animals

Transgenic non-human animals expressing PDGF D hemidimer protein and/or GFD dimer protein are provided according to aspects of the present disclosure. Transgenic non-human animals of the present invention are preferably mice.

Methods and transgenic mice provided by embodiments of the present invention have various utilities such as, but not limited to, in vivo study of bone disorders and treatments therefore.

Transgenic mice are provided according to embodiments of the present invention whose genome includes a nucleic acid encoding PDGF D full-length hemidimer subunit protein and/or GFD subunit protein, wherein the nucleic acid is operably linked to a promoter, and wherein the mouse expresses the encoded protein(s).

Transgenic mice are provided according to embodiments of the present invention whose genome comprises an expression cassette including a nucleic acid encoding PDGF D full-length subunit protein and/or GFD subunit protein, wherein the nucleic acid is operably linked to a promoter and a polyadenylation signal and further contains an intron, wherein the mouse expresses the encoded protein(s).

Any of various methods can be used to introduce a transgene encoding a desired protein or proteins into mice to produce transgenic mice expressing the protein(s). Such techniques are well-known in the art and include, but are not limited to, pronuclear microinjection and transformation of embryonic stem cells. Methods for generating transgenic mice that can be used include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, $3^{rd}$ edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022☐ 15026.

Transgenic mice are provided according to embodiments of the present invention whose genome comprises a nucleic acid encoding PDGF D full-length subunit protein, wherein the nucleic acid is operably linked to a promoter, and wherein the mouse expresses the encoded protein.

Transgenic mice are provided according to embodiments of the present invention whose genome comprises a nucleic acid encoding GFD subunit protein, wherein the nucleic acid is operably linked to a promoter, and wherein the mouse expresses the encoded protein.

Generation of a transgenic mouse expressing PDGF D full-length subunit protein and/or GFD subunit protein can be achieved by methods such as DNA injection of an expression construct into a preimplantation embryo or by use of stem cells, such as embryonic stem (ES) cells or induced pluripotent stem (iPS) cells.

A tissue-specific promoter that can be included in an expression construct for use in generating a transgenic mouse of the present disclosure include, but are not limited to, a promoter that confers bone-specific expression. Bone-specific expression refers to expression of the encoded protein(s) primarily in bone cells with substantially less expression in most other cell types. Bone specific promoters include osteocalcin promoter, dentin matrix protein 1 locus (DMP1) promoter and Prx1 promoter.

A tissue-specific promoter that can be included in an expression construct for use in generating a transgenic mouse of the present disclosure include, but are not limited to, a promoter that confers osteoblast-specific expression. Osteoblast-specific expression refers to expression of the encoded protein(s) primarily in osteoblasts with substantially less expression in most other cell types. An osterix promoter is included in an expression construct to confer osteoblast-specific expression according to aspects of the present disclosure. Osterix promoters are well-known in the art, see for example, Barbuto R. et al., J Mol Endocrinol. 2013; 51(1):99-108, and transgenic mice carrying an Osx1-GFP::Cre transgene are commercially available (The Jackson Laboratory, B6.Cg-Tg(Sp7-tTA,tetO-EGFP/cre)1Amc/J, Stock No: 006361)

Expression in various cell types can be determined quantitatively, e.g., by RT-PCR. Comparison of expression driven by a putative osteoblast-specific promoter with a suitable control, e.g. expression drive by a housekeeping gene promotor, such as beta-actin, is one method that allows for detection of promoters that drive expression primarily in osteoblasts with substantially less expression in most other cell types. According to particular aspects of the present disclosure, osteoblast-specific expression is present where relative expression of a desired transcript in osteoblasts driven by a putative osteoblast-specific promoter is greater than, 1.5-fold, 2-fold, 2.5-fold, 3-fold, 5-fold, 10-fold, or more, compared to at least two other cell types.

For methods of DNA injection of an expression construct into a preimplantation embryo, the expression construct is linearized before injection into non-human preimplantation embryos. Preferably the expression construct is injected into fertilized oocytes. Fertilized oocytes are collected from superovulated females the day after mating (0.5 dpc) and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo: A Laboratory Manual, $3^{rd}$ edition, Cold Spring Harbor Laboratory Press; Dec. 15, 2002, ISBN-10: 0879695919. Offspring can be tested for the presence of the transgene by DNA analysis, such as PCR, Southern blot or sequencing. Mice which are carrying the transgene can be tested for protein expression such as by using ELISA or Western blot analysis.

Alternatively the expression construct may be transfected into stem cells (ES cells or iPS cells) using well-known methods, such as electroporation, calcium-phosphate precipitation and lipofection. The cells are screened for transgene integration by DNA analysis, such as PCR, Southern blot or sequencing. Cells with the correct integration can be tested for functional expression tested by protein analysis for PDGF D full-length subunit protein and/or GFD subunit protein using, for example, ELISA or Western blot analysis.

Mouse ES cells are grown in media optimized for the particular line. Typically ES media contains 15% fetal bovine serum (FBS) or synthetic or semi-synthetic equivalents, 2 mM glutamine, 1 mM Na Pyruvate, 0.1 mM non-essential amino acids, 50 U/ml penicillin and streptomycin, 0.1 mM 2-mercaptoethanol and 1000 U/ml LIF in Dulbecco's Modified Eagle Media (DMEM). Details of such media and growth conditions are known in the art, for example as described in Tremml et al., 2008, Current Protocols in Stem Cell Biology, Chapter 1:Unit 1C.4.

Selected cells incorporating the expression construct can be introduced to produce stem cell chimeras such as described in detail in Manipulating the Mouse Embryo: A Laboratory Manual, $3^{rd}$ edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259: Method for making genetic modifications, U.S. Pat. Nos. 7,659,442, 7,294,754, Kraus et al. 2010, Genesis 48, 394-399).

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation. Chimeric males are selected for breeding. Offspring can be analyzed for transmission of the ES cell genome by coat color and genetic analysis, such as PCR, Southern blot or sequencing. Further the expression of PDGF D full-length subunit protein and/or GFD subunit protein can be analyzed by protein analysis (Western blot, ELISA) or functional assays. Offspring expressing the transgene are intercrossed to create mice homozygous for the transgene. The transgenic mice are backcrossed to create a congenic strain with the PDGF D full-length subunit protein and/or GFD subunit protein transgene.

Methods

As described herein, administration of recombinant and/or isolated PDGF D hemidimer, with or without administration of recombinant and/or isolated GFD dimer, can activate several signaling cascades that improve bone health, such as through the production of osteoprogenitor cells or by accelerating or triggering osteoblast maturation. It is identified herein, that a hemidimer (HD) of one full length PDGF D polypeptide with one GFD polypeptide (CUB domain cleaved) stimulates mesenchymal stem cells to undergo differentiation to osteoprogenitor cells.

Methods according to aspects of the present disclosure include administering a recombinant platelet derived growth factor D (PDGF D) hemidimer to a mesenchymal stem cell or a progenitor derived therefrom, thereby stimulating the mesenchymal stem cell or progenitor cell derived therefrom.

Gene transfer methods can be used to introduce nucleic acids encoding a PDGF D hemidimer and/or a GFD dimer into a subject, such as virus and non-virus based gene transfer methods.

Such methods can be used to administer nucleic acids encoding a PDGF D hemidimer and/or a GFD dimer to cells ex-vivo, or in vivo.

Optionally, a host mesenchymal stem cell or progenitor cell derived therefrom is transfected or infected ex-vivo and then re-introduced into a subject for expression of the encoded protein or proteins in the subject. For example, mesenchymal stem cell or progenitor cell derived therefrom or tissues including such cells may be removed from a subject, transfected or infected with an expression vector encoding a PDGF D hemidimer and/or a GFD dimer and then returned to the subject, such as by systemic administration, e.g. injection, or localized administration, such as implantation for expression of the encoded protein or proteins in the subject. Viral and non-viral vectors including one or more nucleic acids encoding a PDGF D hemidimer and/or a GFD dimer can be delivered in vivo to a subject, or to mesenchymal stem cells, and/or progenitor cells derived therefrom, ex vivo, or such cells in vitro, followed by administration of the treated cells to the subject, such as implantation of the treated cells in the subject for expression of the encoded protein or proteins in the subject.

Mesenchymal stem cells and/or progenitor cells derived therefrom to be treated ex vivo can be obtained from or derived from the subject, such as by biopsy.

Mesenchymal stem cells and/or progenitor cells derived therefrom to be treated in vitro can be cells which are not derived from the subject to be treated, i.e. which may be cells obtained from, or derived from, another individual or group of individuals of the same species, or cells obtained from, or derived from, another individual or group of individuals of a different species.

Non-viral vector delivery methods include administration of DNA plasmids, naked nucleic acid, polycation or lipid:nucleic acid conjugates, naked DNA, naked RNA, artificial virions and nucleic acid associated with a carrier, such as a particle carrier, such as virosomes, liposomes, or immuno-liposomes. Delivery methods for non-viral vectors include, for example, administration by biolistics, electroporation, lipofection, and microinjection.

Virus-based gene transfer methods include viral vectors including DNA and RNA viral vectors.

Optionally, the mesenchymal stem cell or a progenitor derived therefrom is in vitro or in vivo.

In a further option, GFD dimer is also administered to the mesenchymal stem cell or a progenitor derived therefrom, thereby stimulating the mesenchymal stem cell or progenitor cell derived therefrom.

Methods according to aspects of the present disclosure include administering PDGF D hemidimer (HD) to treat a subject in need thereof. According to aspects of the present disclosure, GFD dimer is also administered to the subject.

Methods according to aspects of the present disclosure provide repair and/or regeneration of bone, such as preventing or treating bone conditions, by administering PDGF D hemidimer to a subject in need thereof. According to aspects of the present disclosure, GFD dimer is also administered to the subject.

The administered PDGF D hemidimer may be administered in the form of a protein or as a nucleic acid encoding the PDGF D hemidimer such that the nucleic acid encoding the PDGF D hemidimer is expressed in the subject to produce the nucleic acid encoding the PDGF D hemidimer protein.

The administered GFD dimer may be administered in the form of a protein or as a nucleic acid encoding the GFD dimer such that the nucleic acid encoding the GFD dimer is expressed in the subject to produce the nucleic acid encoding the GFD dimer protein.

Methods according to aspects of the present disclosure provide repair and/or regeneration of bone, such as preventing or treating bone conditions, by administering cells expressing one or more nucleic acids encoding a PDGF D hemidimer and/or a GFD dimer to a subject in need thereof.

The term  subject refers to an individual in need of treatment of viral infection, and generally includes mammals and birds, such as, but not limited to, humans, other primates, cats, dogs, sheep, cows, goats, horses, pigs, poultry, rabbits and rodents, such as rats, mice and guinea pigs. According to aspects of the present disclosure, the subject is human.

The terms  treating and  treatment are used herein to refer to reducing or ameliorating the frequency or severity of at least one sign or symptom of a bone condition inhibited and/or ameliorated by repair and/or regeneration of bone.

A therapeutically effective amount of a composition including a PDGF D hemidimer of the present disclosure is an amount which has a beneficial effect in a subject being treated. In subjects having or at risk of having a bone condition, a therapeutically effective amount of a PDGF D hemidimer is effective to ameliorate one or more signs and/or symptoms of the bone condition wherein the bone condition is inhibited and/or ameliorated by repair and/or regeneration of bone. For example, a therapeutically effective amount of a PDGF D hemidimer composition is effective to stimulate a mesenchymal stem cell or a progenitor derived therefrom, thereby effecting repair and/or regeneration of bone.

A therapeutically effective amount of a composition including a PDGF D hemidimer and GFD dimer of the present disclosure is an amount which has a beneficial effect in a subject being treated. In subjects having or at risk of having a bone condition, a therapeutically effective amount of a PDGF D hemidimer and a GFD dimer is effective to ameliorate one or more signs and/or symptoms of the bone condition wherein the bone condition is inhibited and/or ameliorated by repair and/or regeneration of bone. For example, a therapeutically effective amount of a PDGF D hemidimer composition and a GFD dimer composition is effective to stimulate a mesenchymal stem cell or a progenitor derived therefrom, thereby effecting repair and/or regeneration of bone.

Such bone conditions to be treated include, but are not limited to, bone injury and/or bone loss from any of various causes such as trauma, surgery, aging, and disease, including for example, bone fracture, osteoporosis, dental procedures, surgical procedures, cancer, and metabolic disorder such as, but not limited to hyperparathyroidism.

When administered to a subject, a PDGF D hemidimer and a GFD dimer may be administered simultaneously or separately. According to aspects, a combination of a PDGF D hemidimer and a GFD dimer is administered to a subject simultaneously or separately: (1) via a pharmaceutical composition that includes both a PDGF D hemidimer and a GFD dimer; or (2) co-administration of a PDGF D hemidimer and a GFD dimer wherein the PDGF D hemidimer and the and the GFD dimer have not been formulated in the same composition. When using separate formulations, a PDGF D hemidimer may be administered at the same time, intermittent times, staggered times, prior to, subsequent to, or combinations thereof, with reference to the administration of the GFD dimer.

Pharmaceutical compositions which include a PDGF D hemidimer, and/or one or more nucleic acids encoding PDGF D hemidimer, are provided according to aspects of the present disclosure.

Pharmaceutical compositions which include a PDGF D hemidimer and a GFD dimer, and/or one or more nucleic acids encoding PDGF D hemidimer and a GFD dimer, are provided according to aspects of the present disclosure.

Pharmaceutical compositions which include cells expressing one or more nucleic acids encoding a PDGF D hemidimer and/or a GFD dimer are provided according to aspects of the present disclosure.

A pharmaceutical composition according to aspects of the present disclosure includes a PDGF D hemidimer, and/or one or more nucleic acids encoding PDGF D hemidimer; and a pharmaceutically acceptable carrier.

A pharmaceutical composition according to aspects of the present disclosure includes a PDGF D hemidimer, and/or a GFD dimer; and/or one or more nucleic acids encoding PDGF D hemidimer and/or a GFD dimer; and a pharmaceutically acceptable carrier.

The term "pharmaceutically acceptable carrier" as used herein refers to a carrier or diluent that is generally non-toxic to an intended recipient and which does not significantly inhibit activity of an active agent included in the composition.

A composition according to aspects of the present disclosure generally includes about 0.1-99% of a PDGF D hemidimer, and/or one or more nucleic acids encoding PDGF D hemidimer.

A composition according to aspects of the present disclosure generally includes about 0.1-99% of a PDGF D hemidimer and 0.1-99% of a GFD dimer and/or one or more nucleic acids encoding PDGF D hemidimer and/or a GFD dimer.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions.

Pharmaceutical compositions optionally include a buffer, a solvent, or a diluent.

Examples of suitable aqueous and nonaqueous carriers include water, ethanol, polyols such as propylene glycol, polyethylene glycol and glycerol; vegetable oils such as olive oil; and injectable organic esters such as ethyloleate; and suitable mixtures of any two or more thereof.

Such formulations are administered by a suitable route including parenteral administration. Optionally, administration includes systemic or local administration.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. One or more isotonic agents is optionally included, for example, sugars and or salts such as sodium chloride.

Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, PA, 2006; and Allen, L. V. et al., Ansells Pharmaceutical Dosage Forms and Drug Delivery Systems, 8th Ed., Lippincott, Williams & Wilkins, Philadelphia, PA, 2005.

In particular aspects, a pharmaceutically acceptable carrier included in compositions and/or methods of the present disclosure is a particulate carrier such as lipid particles including liposomes, micelles, unilamellar or mulitlamellar vesicles; polymer particles such as hydrogel particles, polyglycolic acid particles or polylactic acid particles; inorganic particles; and inorganic/organic particulate pharmaceutically acceptable carriers.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm – 10 microns. In particular aspects of the present disclosure, a particulate carrier is formulated such that particles have an average particle size in the range of about 1 nm – 100 nm.

Nanoparticulate formulations of pharmaceutically acceptable carriers included in compositions and/or methods of the present disclosure include, for example, nanoparticulate polymers, dendrimers, liposomes, viruses, carbon nanotubes, and metals such as iron oxide and gold. Exemplary polymers for the preparation of nanoparticles include natural polymers such as heparin, dextran, albumin, gelatin, alginate, collagen, and chitosan or synthetic polymers including polyethylene glycol (PEG), polyglutamic acid (PGA), polylactic acid (PLA), polycarprolactone (PCL) and N-(2-hydroxypropyl)-methacrylamide copolymer (HPMA).

In addition to containing a PDGF D hemidimer and/or a GFD dimer, and/or pharmaceutical compositions including one or more nucleic acids encoding a PDGF D hemidimer and/or a GFD dimer, of the present disclosure, particulate formulations of the disclosure optionally contain any of a variety of useful biologically active molecules and substances including, but not limited to, adjunct therapeutics, proteins, peptides, carbohydrates, oligosaccharides, drugs, and nucleic acids capable of being complexed with the particles.

A PDGF D hemidimer and/or a GFD dimer, and/or pharmaceutical compositions including one or more nucleic acids encoding a PDGF D hemidimer and/or a GFD dimer, of the present disclosure can be associated with particles, for example, by encapsulation in an interior space of the particles, disposed in a lipid domain of the particles, such as a lipid bilayer of liposomes, and/or associated with the particles by binding, such as ionic binding or association by van der Waals forces.

Compositions including a PDGF D hemidimer and/or a GFD dimer, and/or pharmaceutical compositions including one or more nucleic acids encoding a PDGF D hemidimer and/or a GFD dimer, according to aspects of the present disclosure, and a pharmaceutically acceptable carrier, optionally include a lipid-based pharmaceutically acceptable carrier. The term  lipid-based carrier refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions and methods according to aspects of the present disclosure. Compositions including a PDGF D hemidimer and/or a GFD dimer, and/or pharmaceutical compositions including one or more nucleic acids encoding a PDGF D hemidimer and/or a GFD dimer, of the present disclosure, and a pharmaceutically acceptable carrier are provided according to aspects of the present disclosure wherein the pharmaceutically acceptable carrier includes liposomes.

The term  liposome refers to a bilayer particle of amphipathic lipid molecules enclosing an aqueous interior space. Liposomes are typically produced as small unilamellar vesicles (SUVs), large unilamellar vesicles (LUVs) or multilammellar vesicles (MLVs). A PDGF D hemidimer and/or a GFD dimer, and/or one or more nucleic acids encoding a PDGF D hemidimer and/or a GFD dimer, of the present disclosure can be associated with liposomes by encapsulation in the aqueous interior space of the liposomes, disposed in the lipid bilayer of the liposomes and/or associated with the liposomes by binding, such as ionic binding or association by van der Waals forces.

A PDGF D hemidimer and/or a GFD dimer, and/or one or more nucleic acids encoding a PDGF D hemidimer and/or a GFD dimer, of the present disclosure is contained in liposomes when encapsulated in the aqueous interior space of the liposomes, disposed in the lipid bilayer of the liposomes and/or associated with the liposomes by binding, such as ionic binding or association by van der Waals forces. Liposomes according to aspects of the present disclosure are generally in the range of about 1 nanometer  1 micron in diameter although they are not limited with regard to size.

Liposomal formulations of compositions according to aspects of the present disclosure include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy)propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N—(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoylphosphatidylethanolamine (DOPE), distearoylphosphatidylethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term  modified lipid refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000] (DPPE-PEG-2000), and polyethyleneglycol 750 octadecylsphingosine (PEG(750) C8).

In addition to containing a PDGF D hemidimer, pharmaceutical compositions including a PDGF D hemidimer and a GFD dimer, and/or pharmaceutical compositions including one or more nucleic acids encoding a PDGF D hemidimer and/or a GFD dimer, of the present disclosure, liposomes of the disclosure optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term [] biologically active molecules and substances[] refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

According to aspects of the present disclosure, liposomes of the disclosure include a cell-targeting component effective to direct the liposomes to cells. According to aspects of the present disclosure, liposomes of the disclosure include a cell-targeting component effective to direct the liposomes to a specified cell type.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel[]s Pharmaceutical Dosage Forms and Drug Delivery Systems, 8th Ed., Philadelphia, PA: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

Pharmaceutical compositions including a PDGF D hemidimer, pharmaceutical compositions including a PDGF D hemidimer and a GFD dimer, and/or pharmaceutical compositions including one or more nucleic acids encoding a PDGF D hemidimer and/or a GFD dimer, are suitable for administration to a subject by a variety of systemic and/or local routes including, but not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

Pharmaceutical compositions including a PDGF D hemidimer, pharmaceutical compositions including a PDGF D hemidimer and a GFD dimer, and/or pharmaceutical compositions including one or more nucleic acids encoding a PDGF D hemidimer and/or a GFD dimer, and/or cells expressing one or more nucleic acids encoding a PDGF D hemidimer and/or a GFD dimer, are suitable for administration to a subject by implantation of an implant device.

Administration may be to any subject in need of bone repair, bone regeneration or stimulation of mesenchymal stem cells or progenitors derived therefrom.

As the proteins and polypeptides disclosed herein demonstrate significant bone regenerative properties, their administration may occur during surgery to a damaged bone or included in a graft or similar implant to assist in bone regeneration. Administration to a subject may be localized to a site of injury or disrepair or may be systemic or both, either in concert or sequentially.

Compositions of the present disclosure may be administered alone or in concert or sequence with further agents for assisting in bone regeneration including bisphosphates, estrogen, SERMs, parathyroid hormone, alendronate, calcitonin, simvastatin, ibandronate, raloxifine, bazedoxifene, denosumab, risedronate, zoledronate, teriparatide, vitamin D, calcium, vitamin A, collagen, as well as cytokines and growth factors including TGFβ, IL-1, IL-6, PDGF B, VEGF, FGF-1 and -2, and BMP.

Administration may further be with a pharmaceutically acceptable carrier or excipient or diluent, which refers to a non-toxic accompanying salt, sugar, gum, coating or similar. Such are described in Remington: The Science and Practice of Pharmacy ($23^{rd}$ Ed., Academic Press, 2020).

Administration of Pharmaceutical Composition

An inventive composition may be administered acutely or chronically. For example, a composition as described herein may be administered as a unitary dose or in multiple doses over a relatively limited period of time, such as seconds [] hours. In a further embodiment, administration may include multiple doses administered over a period of days [] years, such as for chronic treatment of cancer.

A therapeutically effective amount of a PDGF D hemidimer, a combination of PDGF hemidimer and GFD dimer, and/or pharmaceutical compositions including one or more nucleic acids encoding a PDGF D hemidimer and/or a GFD dimer, and/or cells expressing one or more nucleic acids encoding a PDGF D hemidimer and/or a GFD dimer, will vary depending on the route of administration and form of the composition being administered and the particular composition administered, the severity and type of condition being treated in the subject, the species of the subject, the age and sex of the subject and the general physical characteristics of the subject to be treated. One of skill in the art could determine a therapeutically effective amount in view of these and other considerations typical in medical practice without undue experimentation in view of the present disclosure and what is known in the art. In general, it is contemplated that a therapeutically effective amount of the active agent(s) would be in the range of about 0.001 ng/kg [] 100 mg/kg body weight, optionally in the range of about 0.01 ng/kg [] 1 mg/kg, and further optionally in the range of about 0.1 ng/kg [] 0.1 mg/kg. Further, dosage may be adjusted depending on whether treatment is to be acute or continuing.

Usually between 1 and 100 doses of a composition of the present disclosure are administered to treat a subject in need thereof, although more doses can be given. A composition according to aspects of the present disclosure can be administered twice a day, daily, biweekly, weekly, every other week, monthly or at some other interval, for a treatment course extending one day, 1 week, 2 weeks, 4 weeks, 1 month, 2 months, 3-6 months or longer. A course of treatment is optionally repeated and may extend to chronic treatment if necessary.

Administration of a composition according to aspects of a method of the present disclosure includes administration according to a dosage regimen to produce a desired response. A suitable schedule for administration of doses depends on several factors including age, weight, gender, medical history and health status of the subject, type of composition used and route of administration, for example. One of skill in the art is able to readily determine a dose and schedule of administration for a particular subject.

Methods according to embodiments of the present disclosure include administration of a PDGF D hemidimer, a combination of a PDGF D hemidimer and a GFD dimer, and/or pharmaceutical compositions including one or more nucleic acids encoding a PDGF D hemidimer and/or a GFD dimer, and/or cells expressing one or more nucleic acids encoding a PDGF D hemidimer and/or a GFD dimer, as a pharmaceutical formulation, such as by systemic or local administration.

Exemplary routes of administration include, but are not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

The PDGF D hemidimer, combination of a PDGF D hemidimer and a GFD dimer, and/or pharmaceutical compositions including one or more nucleic acids encoding a PDGF D hemidimer and/or a GFD dimer, and/or cells expressing one or more nucleic acids encoding a PDGF D hemidimer and/or a GFD dimer, may be administered parenterally, for example, by injection such as intraosseal injection, intravenous injection, intramuscular injection, intraperitoneal injection, subcutaneous injection, transdermal injection, intrathecal injection, intracranial injection, intracerebrospinal injection, and/or continuous infusion such as by an intravenous or intracerebrospinal continuous infusion device.

Pharmaceutical compositions including a PDGF D hemidimer, pharmaceutical compositions including a PDGF D hemidimer and a GFD dimer, and/or pharmaceutical compositions including one or more nucleic acids encoding a PDGF D hemidimer and/or a GFD dimer, are administered to a subject by implantation of a drug delivery implant device, preferably an orthopedic implant device, according to aspects of the present disclosure. Such implant devices include a biocompatible matrix and one or more active agents disposed in direct or indirect contact with the matrix.

Pharmaceutical compositions including a cell expressing PDGF D hemidimer, pharmaceutical compositions including a cell expressing PDGF D hemidimer and a GFD dimer, and/or pharmaceutical compositions including a cell expressing one or more nucleic acids encoding a PDGF D hemidimer and/or a GFD dimer, are administered to a subject by implantation of a drug delivery implant device, preferably an orthopedic implant device, according to aspects of the present disclosure. Such implant devices include a biocompatible matrix and one or more active agents disposed in direct or indirect contact with the matrix.

Non-limiting examples of such implant devices include a solid biocompatible matrix in the form of a sponge, mesh, foam, gel, glue, cage, pin, or other orthopedic implant form.

Non-limiting examples of such implant devices include devices which are, or which incorporate, a sponge-like element as the matrix. Examples of such sponge-like implant devices include, but are not limited to, sponges including one or more naturally-occurring and/or synthetic polymers, such as collagen sponges, gelatin sponges, polyvinyl alcohol sponges, chitosan sponges, and cellulose sponges.

In particular aspects, a PDGF D hemidimer, and/or combination of a PDGF D hemidimer and a GFD dimer, pharmaceutical compositions including one or more nucleic acids encoding a PDGF D hemidimer and/or a GFD dimer, and/or cells expressing a PDGF D hemidimer, and/or a combination of a PDGF D hemidimer and a GFD dimer, is/are administered by topical application.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansells Pharmaceutical Dosage Forms and Drug Delivery Systems, $8^{th}$ Ed., Lippincott Williams & Wilkins, 2005, p. 277-297.

In vitro methods according to aspects of the present disclosure are useful, for example, in assessing prevention and/or treatment of particular cells or cell types in isolation.

Combination Treatments

Combinations of therapeutic agents are administered according to aspects of the present disclosure.

In some aspects, a PDGF D hemidimer, combination of a PDGF D hemidimer and a GFD dimer, and/or pharmaceutical compositions including one or more nucleic acids encoding a PDGF D hemidimer and/or a GFD dimer, and at least one additional therapeutic agent are administered to a subject to treat a bone condition in a subject in need thereof.

In still further aspects, a PDGF D hemidimer, combination of a PDGF D hemidimer and a GFD dimer, and/or pharmaceutical compositions including one or more nucleic acids encoding a PDGF D hemidimer and/or a GFD dimer, and at least two additional therapeutic agents are administered to a subject to treat a bone condition in a subject in need thereof.

The term [ additional therapeutic agent[ is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present disclosure include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing a PDGF D hemidimer and/or one or more nucleic acids encoding a PDGF D hemidimer, and one or more additional therapeutic agents may show synergistic effects, e.g., a greater therapeutic effect than would be observed using either the PDGF D hemidimer, and/or nucleic acid encoding the PDGF D hemidimer, or one or more additional therapeutic agents alone as a monotherapy.

Combination therapies utilizing a combination of a PDGF D hemidimer and a GFD dimer, and/or one or more nucleic acids encoding a PDGF D hemidimer and/or a GFD dimer, and one or more additional therapeutic agents may show synergistic effects, e.g., a greater therapeutic effect than would be observed using either the combination of a PDGF D hemidimer and a GFD dimer and/or nucleic acid encoding the PDGF D hemidimer and/or GFD dimer, or one or more additional therapeutic agents alone as a monotherapy.

According to aspects, combination therapies include: (1) pharmaceutical compositions that include a PDGF D hemidimer, and/or GFD dimer, and/or one or more nucleic acids encoding a PDGF D hemidimer and/or a GFD dimer, in combination with one or more additional therapeutic agents;

and (2) co-administration of a PDGF D hemidimer, and/or GFD dimer, and/or one or more nucleic acids encoding a PDGF D hemidimer and/or a GFD dimer, with one or more additional therapeutic agents wherein the PDGF D hemidimer, GFD dimer, and/or one or more nucleic acids encoding a PDGF D hemidimer and/or a GFD dimer, and the one or more additional therapeutic agents have not been formulated in the same composition. When using separate formulations, a PDGF D hemidimer, GFD dimer, and/or one or more nucleic acids encoding a PDGF D hemidimer and/or a GFD dimer, may be administered at the same time, intermittent times, staggered times, prior to, subsequent to, or combinations thereof, with reference to the administration of the one or more additional therapeutic agents.

Combination treatments can allow for reduced effective dosage and increased therapeutic index of a PDGF D hemidimer, and/or GFD dimer, and/or one or more nucleic acids encoding a PDGF D hemidimer and/or a GFD dimer, and the one or more additional therapeutic agents used in methods of the present disclosure.

As noted in the examples, the present disclosure has identified several further features by which the administered compositions achieve their two step processes for differentiation of mesenchymal stem cells to osteoprogenitors to mature osteoblasts. For example, it is believed that the CUB domain is responsible, at least in part, for the HD recruitment and subsequent signaling from TGFβRs. In addition to administration of the CR HD, GFD-D should be administered since HD induces early stages of mesenchymal stem cell differentiation while GFD-D promotes maturation of bone cells.

Inhibition of Adipocyte Differentiation

According to the present disclosure, GFD-D decreases adipocyte differentiation. Thus, according to aspects of the present disclosure, compositions and methods are provided for treating a subject in need of treatment of a condition in which it is advantageous to reduce adipocyte differentiation. Such conditions include metabolic disorders such as, without limitation, diabetes and obesity.

Embodiments of inventive compositions and methods are illustrated in the following examples. These examples are provided for illustrative purposes and are not considered limitations on the scope of inventive compositions and methods.

EXAMPLES

PDGF D Expression

For expression using a vaccinia virus expression system, the nucleotide sequences encoding a PDGF D full length subunit or a GFD subunit are cloned in the pVOTE2 or pVote-JB TEV vector adjacent to the gpt (xanthine guanine phosphoribosyl transferase) gene. Syrian hamster kidney cells of cell line BHK21, are used to produce recombinant PDGF D full length and/or GFD. BHK21 cells are infected with the modified vaccinia Ankara (MVA) for one hour, virus is then removed and cells transfected with the pVOTE2 vector containing PDGF D overnight. Once cytopathic effects are observed (cells rounding up), the culture is freeze-thawed to release the recombinant virus. Recombinant virus is further selected with mycophenolic acid which can only be metabolized by the gpt gene. Protein expression using the recombinant MVA is induced by IPTG and assessed using immunoblotting. Recombinant protein purification is done using a nickel-affinity column.

Serine Proteases Activate Latent Full Length PDGF D Dimer (FL-D) in a 2-Step Manner, Generating Hemidimer (HD) and Growth Factor Domain Dimer (GFD-D)

Serine proteases, such as urokinase-type plasminogen activator (uPA) and matriptase, proteolytically activate latent FL-D into biologically active GFD-D. Utilizing recombinant PDGF D (rPDGF D) that was purified using a vaccinia expression system, it was further shown that PDGF D is a direct substrate for matriptase and identified the serine protease cleavage site at R247/R249 within the hinge region of FL-D. Matriptase processes FL-D into GFD-D in a 2-step manner, generating a 58-kDa intermediate complex, a hemidimer (HD) containing one full-length monomer (FLM) and one GFD monomer (GFD-M) (FIGS. 1A & B).

In this example, PDGF D was expressed in HeLa cells which express matriptase at a high level. Immunoblot analysis in non-reducing condition revealed 3 major dimer species, presumably FL-D, HD, and GFD-D (FIG. 1C). To determine the characteristics of these 3 major dimer species, those three protein bands were isolated by gel extraction, followed by immunoblot analysis under non-reducing and reducing conditions. FL-D contained a 50-kDa FL-M in the reducing condition, as expected (FIG. 1E, lane 3). The HD (FIG. 1E, lane 2) consisted of FL-M and GFD-M, whereas GFD-D (FIG. 1E, lane 1) contained GFD-M. GFD-D, but neither FL-D (lane 1) nor HD (lane 2), was able to activate the classic β-PDGFR dimer-mediated signaling in NIH3T3 fibroblasts (FIG. 1A, the 3rd and bottom panels).

PDGF D, but not PDGF B, Induces hBMSC Differentiation into Osteoblasts (OBs)

The contrasting roles of PDGF B vs. PDGF D on osteoblastic differentiation were demonstrated in human bone marrow mesenchymal stem cells (BMSC) (Lonza, Basel, CH) treated with conditioned medium (CM), collected from LNCaP cells, and engineered to overexpress PDGF B or PDGF D (two ligands for β-PDGFR). CM containing PDGF D, but not PDGF B, was able to induce osteoblast differentiation as determined by alkaline phosphatase (ALP) and Alizarin Red S (ARS) staining (FIGS. 2A & C). The functional significance of PDGF D in CM for OB differentiation was confirmed using a neutralizing antibody (Ab) against PDGF D, whereas the same Ab had no inhibitory effect on BMP4-induced OB differentiation, demonstrating its specificity against PDGF D (FIG. 2B).

Figure 3:
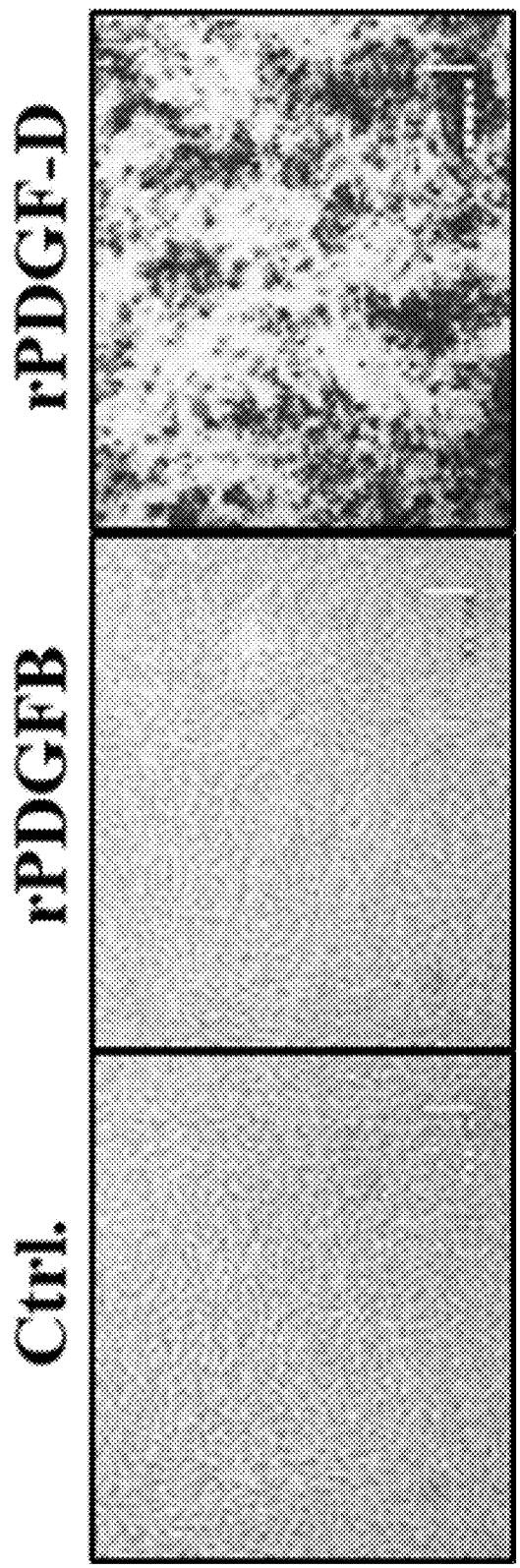
FIG. 3 shows that recombinant PDGF D, but not PDGF B, induces OB differentiation of hMSCs. hMSCs were cultured in osteoblastic inductive medium together with 1 nM PDGF B, or PDGF D for 2 weeks then stained with Alizarin Red S.

Both PDGF B and D were able to activate β-PDGFR in fibroblasts, PDGF D was a far more potent activator of β-PDGFR in BMSCs compared to PDGF B (FIG. 2D). The direct role of PDGF D in osteoblast differentiation was further confirmed using recombinant proteins as shown in FIG. 3.

Figure 4:
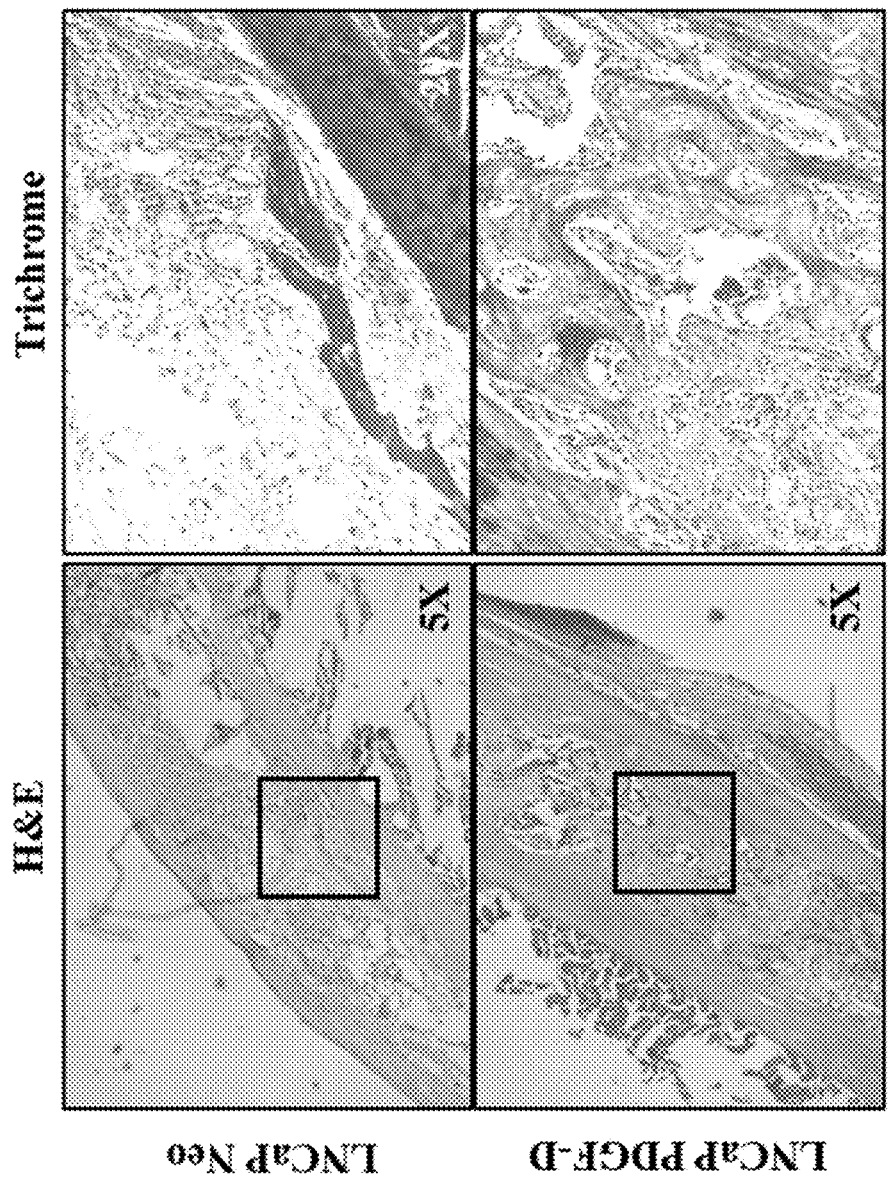
FIG. 4 shows that PDGF D induces new bone formation in mouse tibia. Control vector (Neo) or PDGF D-transfected LNCaP cells were injected into mouse tibia and bone formation was monitored via H&E and Trichrome staining. Area marked with a box in left panels (5×) is shown in right panels (20×)

PDGF D-expressing epithelial cells, or control cells, were injected into tibiae of mice, showing that PDGF D can induce bone formation in vivo. Histopathological analyses showed marked PDGF D-mediated trabecular bone growth with densely deposited bone matrix as shown by dark blue color in trichrome staining of collagen (FIG. 4).

PDGF D HD and GFD-Specific Signal Transduction in hBMSC

To investigate PDGF D dimer-specific signaling programs critical for OB differentiation, wild-type (wt and serine protease cleavage-resistant (CR) FL-PDGF D dimers were generated using a wt or mutant (containing the R247, 249A mutations in the serine protease cleavage site in the hinge region) FL-D expression vector, respectively. GFD-D was generated using a GFD expression vector. CR-HD was generated as summarized in FIG. 5. It was confirmed that CR-FL-D and CR-HD do not undergo proteolytic cleavage by serine proteases, ensuring that CR-FL-D can be used as a negative control and CR-HD signaling does not result from its conversion to GFD-D by pericellular serine proteases. Consistent with FIG. 2, purified GFD-D activated β-PDGFR far more effectively than PDGF B in BMSCs, while both activated β-PDGFR equally well in fibroblasts (FIGS. 6A & B). Among signaling molecules tested for differential activation between PDGF B vs. D, Akt and p38 were readily activated upon 10 min-treatment with GFD-D (FIG. 6A).

Figure 7:
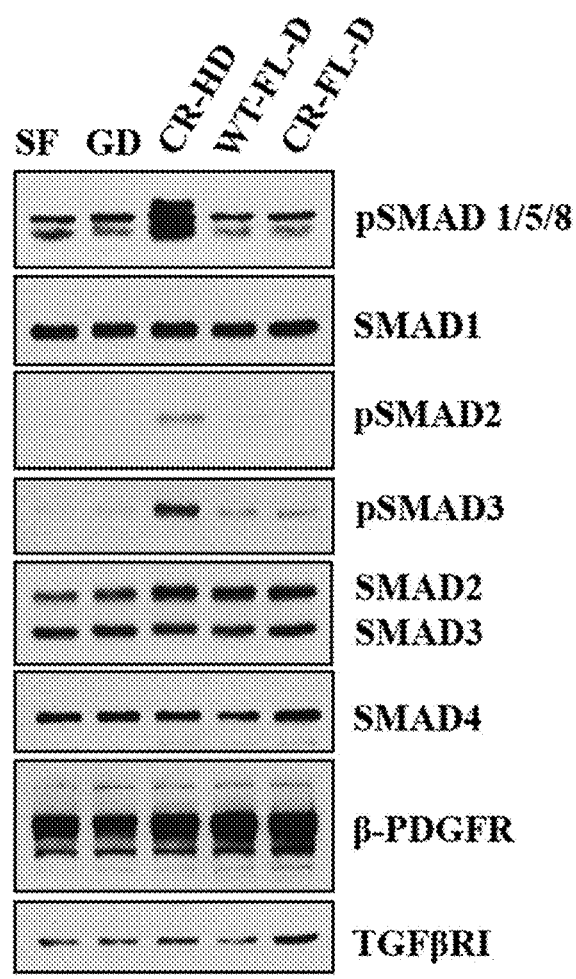
FIG. 7 shows PDGF D HD activates SMADs in hBMSC. Serum starved hBMSCs were treated with the indicated PDGF ligand for 60 minutes. Immunoblot analysis was performed with the indicated antibodies.

SMAD2, SMAD3, and SMAD1/5/8 were prominently activated post 60 min-treatment of BMSCs in an HD-specific manner (FIG. 7). These results demonstrated the novel signaling capacity of PDGF D HD and GFD-D in BMSCs.

PDGF D Inhibits hBMSC Differentiation into Adipocytes.

To determine the role of PDGF D in adipogenesis, hBMSC was cultured in adipogenic induction media in the presence or absence of recombinant PDGF D (rPDGF D) proteins. As shown in FIG. 8, PDGF D served as a potent inhibitor of adipogenesis as determined by staining lipid droplets with Oil Red O. PDGF D effectively downregulated the expression of PPARg and C/EBPa, well-known adipogenic transcription factors, as well as fatty acid synthase, fatty acid binding protein 4 (FABP4), acetyl-CoA-carboxylase (ACC) and perilipin 1, critical for fatty acid synthesis and/or storage.

Results of the disclosure show that the PDGF D hemidimer (HD) promotes BMSC commitment to osteoprogenitor cells via its induction of the β-PDGFR/TGFbR/SMADs signaling network leading to induction of osteogenic transcription factors such as Runx2. Further, growth factor domain dimer (GFD-D) signaling induces osteoblast maturation involving the recruitment of E3 ubiquitin-protein ligase HUWE1 in the β-PDGFR singling complex, resulting in osteoblastic signal transduction, whereas it downregulates adipogenic signaling pathways (FIG. 9).

Structure-Function Relationship of the CUB Domain of PDGF D for the Recruitment of TGFβR Analysis of amino acid sequences showed ~35% identity and 65% similarity between the CUB domain of PDGF D and the prototypical CUB domain of NRP-1 (FIG. 10). While most CUB domains contain 4 cysteines that form 2 disulfide bonds, the CUB domain in PDGF D contains only two cysteines (see FIG. 10). Similarly, the CUB domain in MASP (serum mannose-binding proteins-associated serine proteases) contains only 2 cysteines and its crystal structure showed one disulfide bridge, resulting in a slightly less compact ellipsoidal β-sandwich structure, see also Feinberg, H., et al., EMBO J, 2003. 22(10): p. 2348-59.

Matriptase cleavage in the hinge region of one subunit of PDGF D dimer was shown to generate HD, removing one CUB domain in the non-reducing condition. This suggests that 2 cysteines in the CUB domain are likely to form an intrachain disulfide bridge, not an interchain bridge between the CUB domains. Since the CUB domain is known to mediate protein-protein interactions and the disulfide bonds in the CUB domain are critical to maintain the ellipsoidal β-sandwich structure, the cysteine residues can be mutated to alanine (C58A and C80A, individually or in combination). Stable CR-HD containing wild type CUB domain (CR-wtHD) or mutated CUB domain (CRmtCUB-HD) can be purified as described in FIG. 5. The ability of wtHD and mtCUB-HD to interact with TGFβR is examined by immunoprecipitation using anti-His tag antibody (that recognizes His-tagged HD) followed by immunoblot analysis using anti-TGFβRI or TGFbRII antibodies, or vice versa. The presence of β-PDGFR in anti-His tag immune complexes (wtHD or mtCUB-HD complexes), and activation (phosphorylation) of TGFbR/SMADs are determined.

Figure 11:
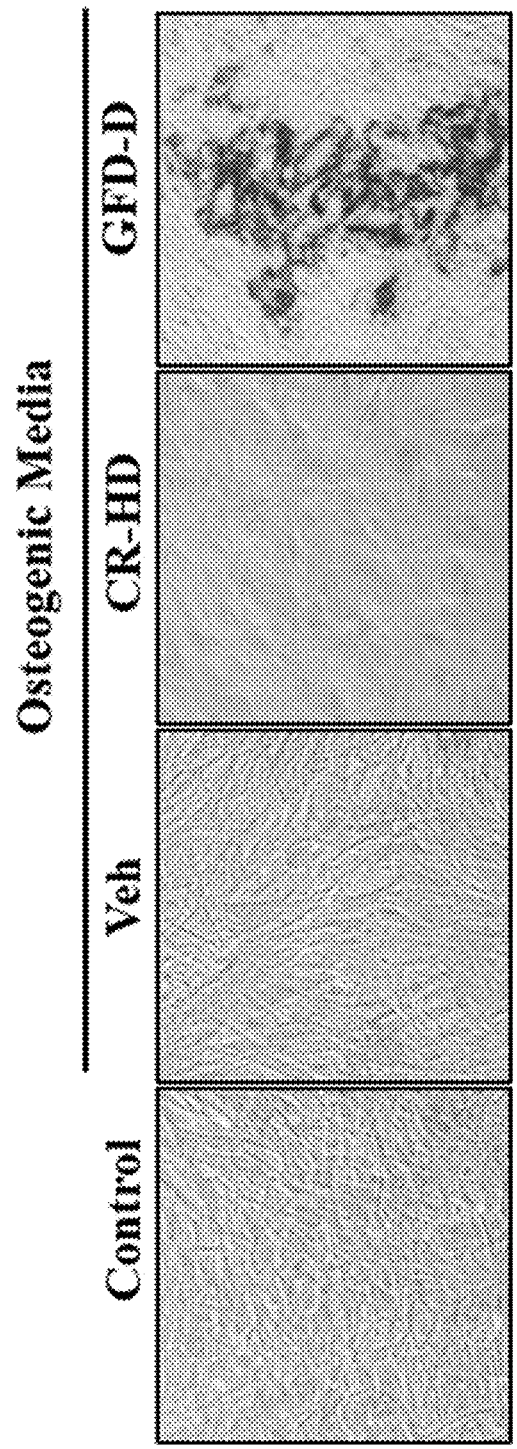
FIG. 11 shows PDGF D HD treatment alone is insufficient for OB maturation and GFD-D promotes OB maturation. hBMSCs, committed into osteoprogenitors by culturing in osteogenic media, were treated with control solution (veh), 0.5 nM CR-HD or 0.5 nM GFD-D for 9 days before ARS staining GFD.

Examination of PDGF D GFD-Specific β-PDGFR Signaling Program Critical for Osteoblast Maturation HD treatment alone was insufficient to induce osteoblastogenesis (FIG. 11), suggesting the involvement of GFD-D signaling in OB maturation. Indeed, osteoblast maturation was greatly promoted by GFD-D (FIG. 11). Taken together, it is believed that PDGF D induces osteoblastic signaling programs in a 2-step manner: HD induces TGFβR/SMAD signaling for the early steps of OB differentiation, and pericellular serine protease-mediated further cleavage of HD into GFD-D contributes to OB maturation (FIG. 9).

PDGF D Compositions as an Inducer of Bone Formation/Regeneration in Preclinical Animal Models As described herein, PDGF D serves as a potent osteogenic factor especially at the site of injury through coordinated HD- and GFD-D-specific osteogenic signal transduction. In this example, transgenic mouse models are generated to demonstrate efficacy of PDGF D in maintaining bone with aging and/or promoting bone formation/regeneration upon injury.

Further demonstrated is efficacy of recombinant PDGF D proteins (rPDGF D) in a murine femoral defect/repair model. Delivery of rPDGF D via an implanted FDA-approved absorbable gelatin sponge, demonstrates the efficacy of rPDGF D in bone regeneration.

Generation of Transgenic Mice Expressing Osteoblast (OB)-Specific PDGF D and Examination of its Effects on Age-Related Bone Changes A conditional overexpression system described in detail in Chu, V. T., et al., BMC Biotechnol, 2016. 16: p. 4, is adapted for used with PDGF D. Tissue specific expression of PDGF D is accomplished using a conditional overexpression system in this example. The ROSA26 targeting vector is used to clone murine PDGF D downstream of the floxed stop cassette driven by the CAG promoter. The presence of the Cre recombinase removes the stop cassette leading to the expression of PDGF D. ROSA26 knockin mice are then mated with osterix-Cre (Osx-Cre) mice (commercially available mouse line at Jackson Labs Strain ID 006361) to generate the Osx-Cre;Pdgfd mouse leading to osteoblast-specific PDGF D expression Evaluation of the Effects of PDGF D on Bone Regeneration/Healing in Old Mice To evaluate the role of PDGF D on bone healing at the injury site of old bone, bone fractures are created in legs of 25 months old WT and PDGF D transgenic mice using a device that uses a sliding weight and guillotine mechanism. This device consistently produces controlled displacement and high-energy impact force sufficient for induction of fractures in mouse tibias. The impact velocity is recorded for each group and can serve an indicator of force needed to cause bone fracture. Mice are euthanized 10, 20, or 40 days post bone fracture for outcome analysis. Micro-computed tomography (μCT) imaging analysis is performed to assess bone fracture healing by measuring bone volume, bone volume fraction, and trabecular thickness. Mechanical properties of fractures are also measured at 10, 20 and 40 days post bone fracture. Hematoxylin and Eosin (H&E), Safranin-O, and Masson[]s Trichrome staining are performed on longitudinal sections. Bone histomorphometric analysis is also performed to examine area of total callus, chondrocyte (Safranin-O positive area), and new bone.

Generation of Transgenic Mice Expressing OB-Specific PDGF D in an Inducible Manner and Examination of its Effects on Age-Related Bones Transgenic mice constitutively expressing OB-specific PDGF D are useful to examine whether PDGF D signaling prevents age-associated bone loss and to test its effects on bone fracture healing. To test the direct effects of PDGF D, transgenic mice expressing PDGF D in a bone- and temporal-specific manner are generated as described herein. The PDGF D transgenic mice are mated to transgenic mice expressing a tamoxifen inducible Cre recombinase driven by the mouse Col1a1 (collagen, type I, alpha 1) promoter (commercially available mouse line at Jackson Labs Strain ID 016241). Tamoxifen administration induces Cre recombination in the osteoblasts of most bones. 25-month old Col1a1-CreERT2-PDGF D or wild-type littermates (10 mice in each group) are injected intraperitoneally with 0.75 mg of 4-hydroxytamoxifen for 5 consecutive days. Forty-eight hours after the final injection, tibial fractures can then immediately be created as described above. Mice are euthanized 10, 20, or 40 days post bone fracture and the outcome analyses are performed as described above. IHC analysis is performed to confirm PDGF D overexpression and detect active (phosphorylated) β-PDGFR, SMADs, Akt as well as increased expression levels of PDGF D regulated osteoblastic transcription factors (identified above).

Evaluation of the Therapeutic Efficacy of Recombinant PDGF D Proteins (rPDGF D) in an Aged Mouse Femoral Bone Repair Model of Aged Bone PDGF D is identified herein as an inducer of bone formation via HD and GFD-D-specific osteoblastic signal transduction, see FIG. 9. The therapeutic efficacy of rPDGF D using a murine femoral defect model is compared to the current treatment regimens; BMP2 and PDGF B, individually or in combination. Femoral defect is created by craniolateral incision and blunt dissection between the Rectus femoris and Vastus lateralis muscles in 25 months old mice. Femurs are elevated using forceps and through-and-through window defects are created in the distal metaphysis 5 mm proximal to the femoral trochleae using a Dremel 8100 with a 0.75 mm drill bit. Prior to surgeries, US FDA-approved absorbable gelatin sponges (Pfizer Gelfoam 12□ 7 mm) are incubated for 45 min in 15 µL of PBS (vehicle control), 5 g (12.8 µM) rBMP-2, 1 g (2.74 µM) rPDGF B, 5 g rBMP-2 & 1 g rPDGF B, or 1.32 µg (2.74 µM) rPDGF D in PBS. Defects are plugged with collagen grafts from each group (total 5 groups). 20 mice in each group will receive femoral defects and 10 mice are then analyzed at day 10 and the other 10 mice at day 20. Micro-computed tomography (µCT) imaging analysis is performed to assess bone regeneration by measuring bone volume, bone volume fraction, and trabecular thickness. Mechanical properties and bone histomorphometric analyses are also performed as described above. IHC analysis is performed to detect active (phosphorylated) β-PDGFR, SMADs, Akt as well as increased expression levels of PDGF D-regulated osteoblastic transcription factors (identified above).

FIGURES

Figure 1B:
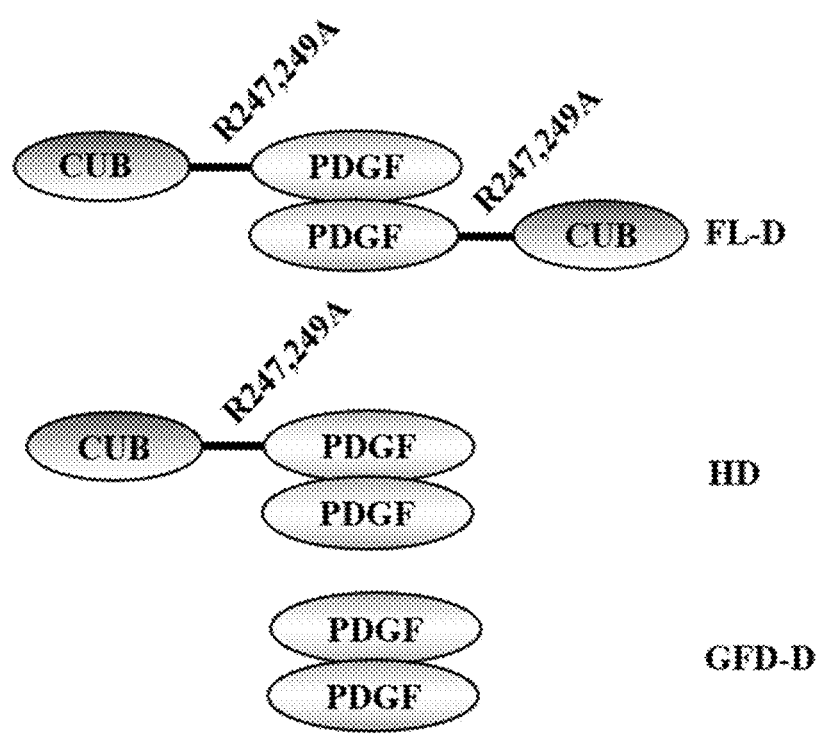
Figures 1C, 1D, 1E:
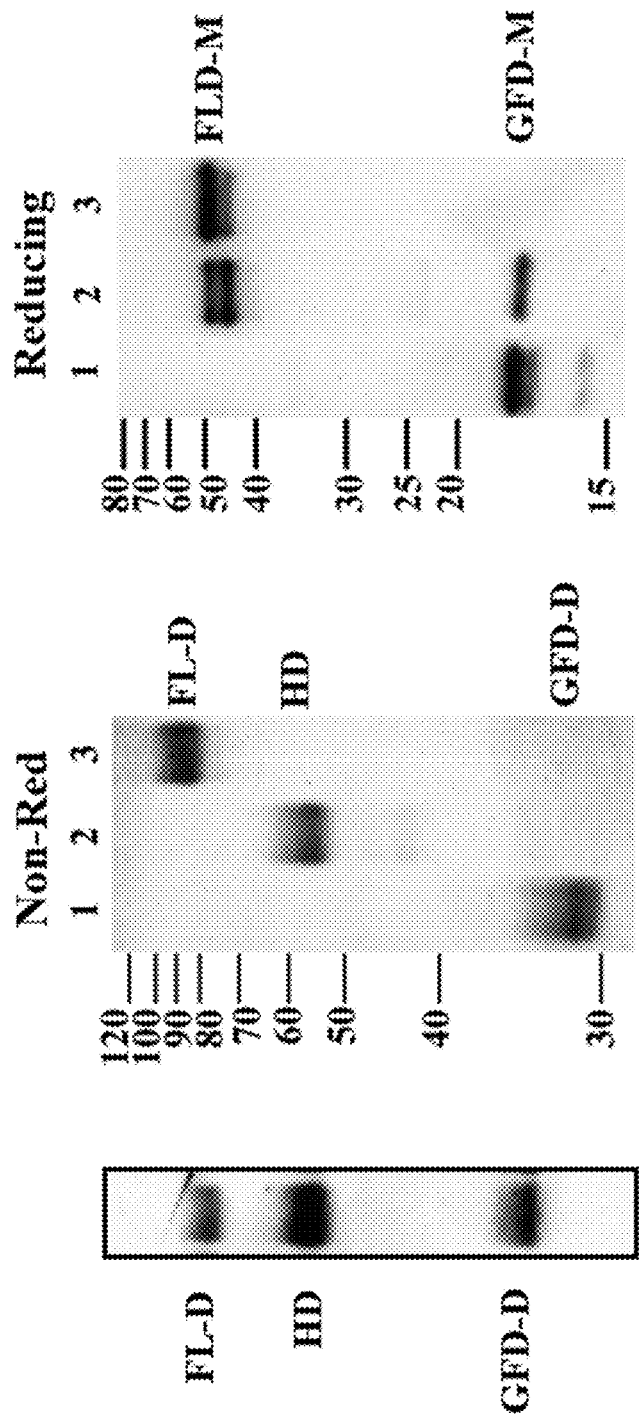

FIG. 1 shows characterization of PDGF D dimer species. FIG. 1A shows an immunoblot analysis of rPDGF D processed by increasing concentrations of matriptase in nonreducing (top) and reducing (middle) conditions and its activation of β-PDGFR in NIH3T3 cells (bottom 2 panels) FIG. 1B shows schematic diagram of FL-D, hemidimer (HD) and GFD-D; R247, R249 in the serine protease cleavage site in the hinge region. FIGS. 1C-E PDGF D dimer species (FL-D, HD, and GFD-D) were extracted from a non-reducing SDS-PAGE gel (C), resolved on non-reducing (D) and reducing SDS-PAGE gel (E).

FIG. 2 shows PDGF D induces osteoblastic differentiation. hBMSCs were treated with equal micrograms of LNCaP-derived conditioned medium in medium containing 50 µg/ml ascorbic acid, 10 mM β-glycerolphosphate, 100 nM dexamethasone. FIG. 2A shows alkaline phosphatase (ALP) activity assay and Alizarin Red S (ARS) staining, markers for osteoblastogenesis. FIG. 2B shows hBMSCs were treated with 200 ng/ml BMP-4 or 2 µg/ml concentrated CM from indicated LNCaP cells in the presence or absence of 2 µg/ml neutralizing antibody against PDGF D (αD Ab), then ALP activity was determined. FIG. 2C shows immunoblot analysis of PDGF B and PDGF D using indicated CM. FIG. 2D shows the β-PDGFR activation assay in serum-starved NIH3T3 cells or hBMSCs using serum-free (SF) media, or CM from control (Neo), PDGF B- or PDGF D-transfected LNCaP.

FIG. 3 shows that recombinant PDGF D, but not PDGF B, induces OB differentiation of hMSCs. hMSCs were cultured in osteoblastic inductive medium together with 1 nM PDGF B, or PDGF D for 2 weeks then stained with Alizarin Red S.

FIG. 4 shows that PDGF D induces new bone formation in mouse tibia. Control vector (Neo) or PDGF D-transfected LNCaP cells were injected into mouse tibia and bone formation was monitored via H&E and Trichrome staining. Area marked with a box in left panels (5×) is shown in right panels (20×).

Figure 5:
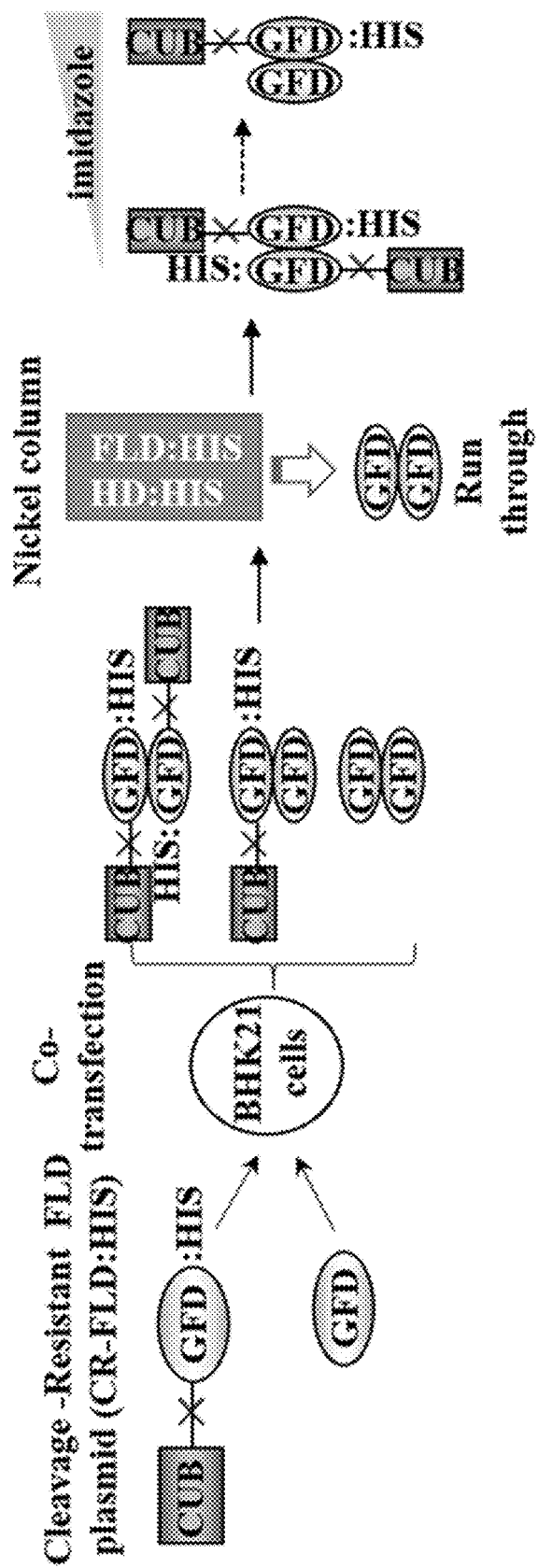
FIG. 5 shows production of cleavage-resistant, stable HD (CR-HD). CR-HD was produced through co-transfection of cleavage resistant (R247,249A) full-length PDGF D:His (CR-FL-D) and PDGF D growth factor domain (D235-R370) constructs in a 1:5 ratio. CM was collected and run through Nickel (His-TRAP, GE Biosciences) column.
Figure 6A:
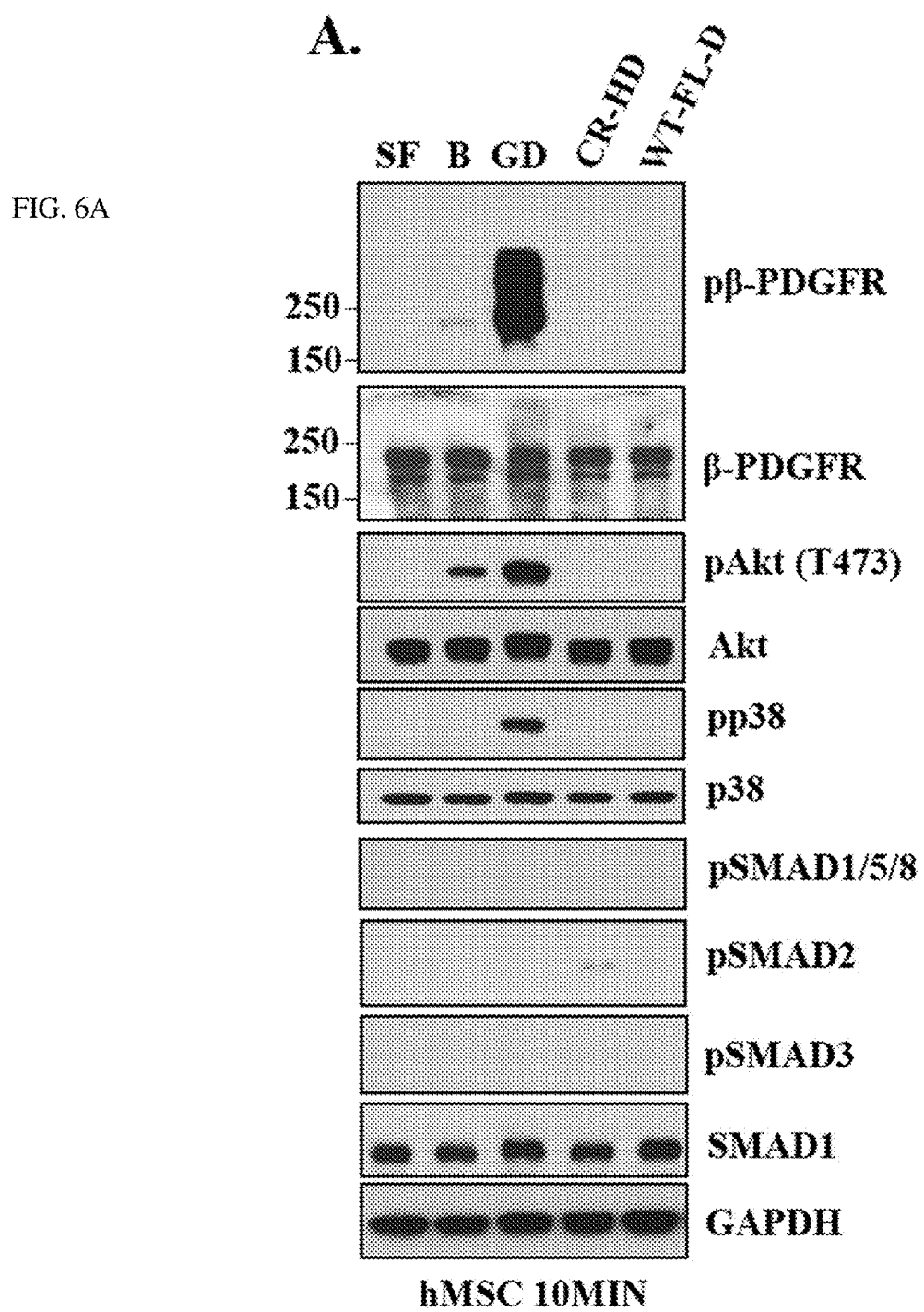
FIGS. 6A-6B show differential signaling capacity of PDGF D dimer species in hBMSCs.

FIG. 5 shows production of cleavage-resistant, stable HD (CR-HD). CR-HD was produced through co-transfection of cleavage resistant (R247,249A) full-length PDGF D:His (CR-FL-D) and PDGF D growth factor domain (D235-R370) constructs in a 1:5 ratio. CM was collected and run through Nickel (His-TRAP, GE Biosciences) column.

Figure 6B:
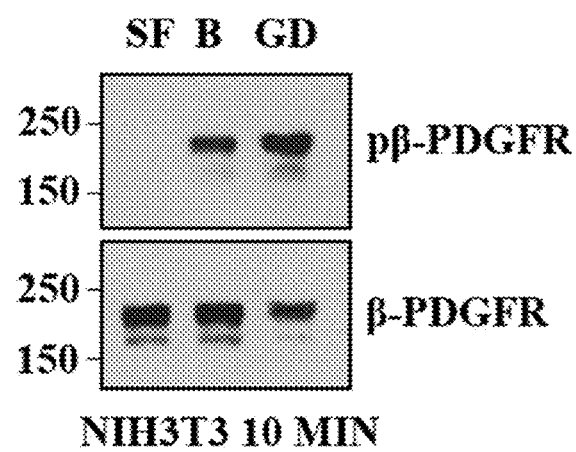

FIG. 6 shows differential signaling capacity of PDGF D dimer species in hBMSCs. FIG. 6A shows serum starved hBMSC were treated with indicated PDGF ligand for 10 minutes. Immunoblot analysis was performed with the indicated Abs. FIG. 6B shows the β-PDGFR activation assay in serum starved NIH3T3 upon 10 min treatment with PDGF B or PDGF D GFD.

FIG. 7 shows PDGF D HD activates SMADs in hBMSC. Serum starved hBMSCs were treated with the indicated PDGF ligand for 60 minutes. Immunoblot analysis was performed with the indicated antibodies.

Figure 8A:
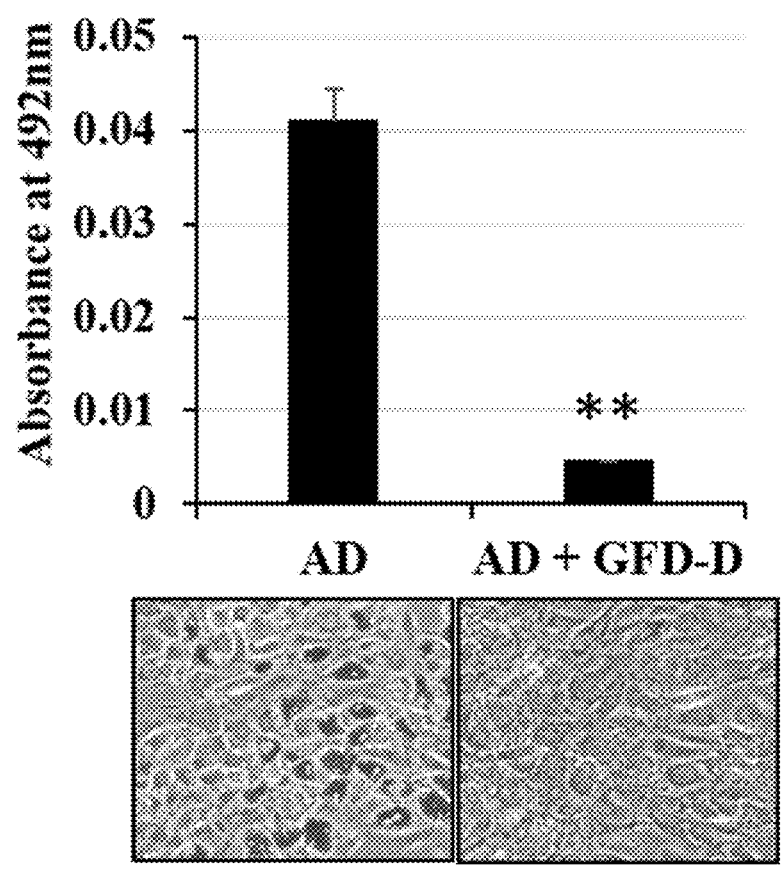
FIGS. 8A and 8B show PDGF D inhibits hBMSC differentiation into adipocytes.
Figure 8B:
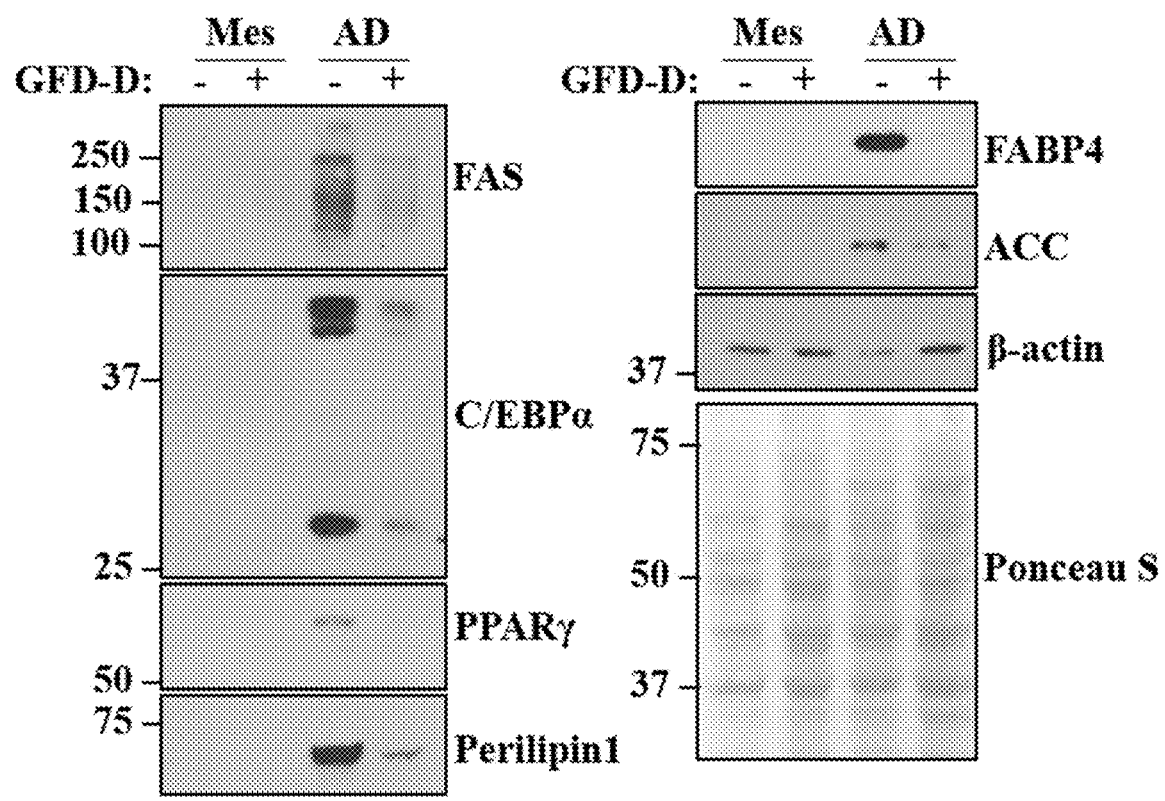

FIG. 8 shows PDGF D inhibits hBMSC differentiation into adipocytes. FIG. 8A shows hBMSCs were induced to differentiate into adipocytes using adipogenic media (AD) with and without 1 nM GFD-D for 2 weeks then lipid droplets stained with Oil Red O and quantified. FIG. 8B shows hBMSCs were grown under normal growth (Mes) or adipogenic (AD) conditions in the presence or absence of 1 nM GFD for two weeks. Cell lysates were subjected to immunoblot analysis for adipogenic markers.

FIG. 9 shows a working model for PDGF D dimer-specific regulation of osteoblastogenic differentiation of BMSC.

FIG. 10 shows alignment of CUB domains. Amino acid sequences of CUB domain of PDGF D, BMP1 (Bone Morphogenetic Protein 1), NRP1 (Neuropilin 1), and SCUBE3 (Signal Peptide, CUB Domain and EGF-Like Domain Containing 3) were aligned. The 4 consensus cysteines are boxed.

FIG. 11 shows PDGF D HD treatment alone is insufficient for OB maturation and GFD-D promotes OB maturation. hBMSCs, committed into osteoprogenitors by culturing in osteogenic media, were treated with control solution (veh), 0.5 nM CR-HD or 0.5 nM GFD-D for 9 days before ARS staining GFD.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

What is claimed is:

1. A pharmaceutical composition for stimulating bone growth or inhibiting adipocytes, comprising:
   1) an isolated recombinant platelet-derived growth factor D (PDGF D) wild-type hemidimer or isolated recombinant cleavage resistant-hemidimer (CR-HD), 2) an isolated recombinant growth factor domain (GFD) dimer; and 3) a pharmaceutically acceptable carrier, wherein 1) and 2) are separate moieties.

2. The pharmaceutical composition of claim 1, wherein the isolated recombinant CR-HD comprises:
   a recombinant polypeptide with at least 85% identity to the amino acid sequence set forth in SEQ ID NO: 5, wherein at least one of positions 247 or 249 is a non-charged amino acid.

3. The pharmaceutical composition of claim 2, wherein both positions 247 and 249 are non-charged amino acids.

4. The pharmaceutical composition of claim 1, wherein the isolated recombinant GFD dimer comprises a recombinant polypeptide with at least 85% identity to the amino acid sequence set forth in SEQ ID NO: 3 or SEQ ID NO:7, and optionally includes a mutation in any one, two, or all three of $R^{340}$, $R^{341}$ and $R^{343}$.

5. A composition for stimulating bone growth or inhibiting adipocytes, comprising:
   a nucleic acid encoding the PDGF D full length subunit polypeptide included in the hemidimer of claim 1, and a nucleic acid encoding the GFD subunit polypeptide included in the GFD dimer of claim 1.

6. A method of treating a subject in need thereof, comprising: administering a recombinant platelet derived growth factor D (PDGF D) composition to a mesenchymal stem cell of the subject and/or a progenitor derived therefrom, producing a treated mesenchymal stem cell of the subject and/or a progenitor derived therefrom, thereby stimulating the mesenchymal stem cell and/or a progenitor derived therefrom, and wherein the PDGF D composition comprises 1) an isolated recombinant platelet-derived growth factor D (PDGF D) wild-type hemidimer or isolated recombinant cleavage resistant-hemidimer (CR-HD) and 2) an isolated recombinant growth factor domain (GFD) dimer, wherein 1) and 2) are separate moieties.

7. The method of claim 6, wherein the subject is in need of bone repair, bone regeneration, or adipocyte inhibition.

8. The method of claim 6, wherein the GFD lacks a CUB domain.

9. The method of claim 6, wherein the full-length PDGF D comprises an amino acid sequence with at least 85% sequence identity to SEQ ID NO: 1 or SEQ ID NO: 5.

10. The method of claim 6, wherein the GFD comprises an amino acid sequence with at least 85% sequence identity to SEQ ID NO: 3 or SEQ ID NO: 7, and optionally includes a mutation in any one, two, or all three of $R^{340}$, $R^{341}$ and $R^{343}$.

11. The method of claim 6, wherein the PDGF D hemidimer is administered by introducing a polynucleotide encoding PDGF D full length subunit and a polynucleotide encoding PDGF D GFD to the mesenchymal stem cell and/or progenitor derived therefrom, wherein the mesenchymal stem cell and/or progenitor derived therefrom translates the polynucleotide or produces a transcript thereof, whereby the PDGF D hemidimer is produced in the mesenchymal stem cell and/or progenitor derived therefrom.

12. The method of claim 6, wherein the GFD dimer is administered by introducing a polynucleotide encoding a PDGF D GFD to the mesenchymal stem cell and/or progenitor derived therefrom, wherein the cell translates the polynucleotide and/or produces a transcript thereof, whereby the GFD dimer is produced in the mesenchymal stem cell and/or progenitor derived therefrom.

13. The method of claim 6, wherein the subject in need of adipocyte inhibition has age-associated bone loss with increased adipogenesis.

14. The method of claim 6, wherein the mesenchymal stem cell and/or the progenitor derived therefrom is treated with the recombinant PDGF D composition and/or engineered to express the recombinant PDGF D composition.

15. The method of claim 14, wherein the mesenchymal stem cell and/or the progenitor derived therefrom is in-vitro or ex-vivo and further comprising administering the treated mesenchymal stem cell of the subject and/or a progenitor derived therefrom to the subject.

16. The method of claim 15, wherein administering the treated mesenchymal stem cell of the subject and/or a progenitor derived therefrom to the subject comprises administration at a site of injury or disease.

* * * * *